(12) United States Patent
Lange et al.

(10) Patent No.: US 11,865,219 B2
(45) Date of Patent: *Jan. 9, 2024

(54) PEROXYCARBOXYLIC ACID BASED SANITIZING RINSE ADDITIVES FOR USE IN WARE WASHING

(71) Applicant: ECOLAB USA INC., Saint Paul, MN (US)

(72) Inventors: Steven J. Lange, Saint Paul, MN (US); Junzhong Li, Saint Paul, MN (US); Xin Sun, Saint Paul, MN (US); Allison Brewster, Saint Paul, MN (US); Richard Staub, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/305,857

(22) Filed: Jul. 15, 2021

(65) Prior Publication Data

US 2021/0353800 A1 Nov. 18, 2021

Related U.S. Application Data

(63) Continuation of application No. 13/863,001, filed on Apr. 15, 2013, now abandoned.

(51) Int. Cl.
*A61L 2/18* (2006.01)
*A01N 37/02* (2006.01)
(Continued)

(52) U.S. Cl.
CPC ............. *A61L 2/186* (2013.01); *A01N 37/02* (2013.01); *A01N 37/16* (2013.01); *A01N 59/00* (2013.01); *A61L 2/18* (2013.01)

(58) Field of Classification Search
CPC ........... A61L 2/186; A61L 2/18; A01N 37/02; A01N 37/16; A01N 59/00
See application file for complete search history.

(56) References Cited

U.S. PATENT DOCUMENTS

| 1,772,975 | A | 8/1930 | Wieland |
| 2,012,021 | A | 8/1932 | Petersen |

(Continued)

FOREIGN PATENT DOCUMENTS

| AU | 199911969 B2 | 4/1999 |
| AU | 200185520 A1 | 1/2002 |

(Continued)

OTHER PUBLICATIONS

US 7,851,571 B2, 12/2010, Rodrigues et al. (withdrawn)

(Continued)

*Primary Examiner* — Trevor Love
(74) *Attorney, Agent, or Firm* — McKee, Voorhees & Sease, PLC

(57) ABSTRACT

A concentrated liquid sanitizing and rinse composition containing peroxycarboxylic acid(s) and compatible rinse aid surfactants is disclosed. The sanitizing and rinsing compositions are formulated in a single liquid concentrate, replacing a traditional dual product of a sanitizer and rinse aid. The sanitizing and rinsing chemistries are particularly effective at neutral pHs against gram negative organisms at elevated temperatures. Methods of using the concentrated liquid sanitizing and rinse composition are also disclosed.

13 Claims, 5 Drawing Sheets

(51) Int. Cl.
*A01N 37/16* (2006.01)
*A01N 59/00* (2006.01)

(56) References Cited

U.S. PATENT DOCUMENTS

| | | |
|---|---|---|
| 2,466,663 A | 4/1949 | Russ |
| 2,512,640 A | 6/1950 | Greenspan et al. |
| 2,592,884 A | 4/1952 | Fox et al. |
| 2,592,885 A | 4/1952 | Fox et al. |
| 2,592,886 A | 4/1952 | Fox et al. |
| 2,833,813 A | 5/1958 | Wallace |
| 3,044,092 A | 7/1962 | Fox et al. |
| 3,122,417 A | 2/1964 | Blaser et al. |
| 3,146,718 A | 9/1964 | Fox et al. |
| 3,248,281 A | 4/1966 | Goodenough |
| 3,272,899 A | 9/1966 | Diamond et al. |
| 3,297,456 A | 1/1967 | Newell |
| 3,329,615 A | 7/1967 | Cooper |
| 3,350,265 A | 10/1967 | Rubinstein et al. |
| 3,370,597 A | 2/1968 | Fox |
| 3,444,242 A | 5/1969 | Rue |
| 3,514,278 A | 5/1970 | Brink, Jr. |
| 3,580,850 A | 5/1971 | Dupre |
| 3,592,774 A | 7/1971 | Altenschopfer |
| 3,620,786 A | 11/1971 | Hatch |
| 3,625,901 A | 12/1971 | Rue |
| 3,650,965 A | 3/1972 | Cantor |
| 3,858,854 A | 1/1975 | Win et al. |
| 3,867,300 A | 2/1975 | Karabinos et al. |
| 3,874,927 A | 4/1975 | Willard, Sr. |
| 3,890,350 A | 6/1975 | Hardtmann |
| 3,895,116 A | 7/1975 | Herting et al. |
| 3,908,680 A | 9/1975 | Krezanoski |
| 3,910,880 A | 10/1975 | Lamberti |
| 3,915,633 A | 10/1975 | Ramachandran |
| 3,929,678 A | 12/1975 | Laughlin et al. |
| 3,941,713 A | 3/1976 | Dawson et al. |
| 3,944,497 A | 3/1976 | Alterman et al. |
| 3,960,781 A | 6/1976 | Freis et al. |
| 3,996,386 A | 12/1976 | Malkki et al. |
| 4,002,775 A | 1/1977 | Kabara |
| 4,005,024 A | 1/1977 | Rodriguez et al. |
| 4,011,346 A | 3/1977 | Ernst |
| 4,024,257 A | 5/1977 | Kibbel, Jr. |
| 4,041,149 A | 8/1977 | Gaffar et al. |
| 4,051,058 A | 9/1977 | Böwing et al. |
| 4,051,059 A | 9/1977 | Böwing et al. |
| 4,094,953 A | 6/1978 | Hadi et al. |
| 4,129,517 A | 12/1978 | Eggensperger et al. |
| 4,136,052 A | 1/1979 | Mazzola |
| 4,147,559 A | 4/1979 | Fraula et al. |
| 4,162,987 A | 7/1979 | Maguire, Jr. et al. |
| 4,187,121 A | 2/1980 | Herold et al. |
| 4,190,551 A | 2/1980 | Murata et al. |
| 4,191,660 A | 3/1980 | Schreiber et al. |
| 4,203,756 A | 5/1980 | Claeys et al. |
| 4,219,435 A | 8/1980 | Biard et al. |
| 4,219,436 A | 8/1980 | Gromer |
| 4,244,884 A | 1/1981 | Hutchins et al. |
| RE30,537 E | 3/1981 | Fraula et al. |
| 4,253,842 A | 3/1981 | Ehrlich |
| 4,285,352 A | 8/1981 | McMahon et al. |
| 4,289,728 A | 9/1981 | Peel et al. |
| 4,321,157 A | 3/1982 | Harris et al. |
| 4,370,199 A | 1/1983 | Orndorff |
| 4,376,787 A | 3/1983 | Lentsch et al. |
| 4,404,040 A | 9/1983 | Wang |
| 4,406,884 A | 9/1983 | Fawzi et al. |
| 4,410,442 A | 10/1983 | Lucas et al. |
| 4,411,810 A | 10/1983 | Dutton et al. |
| 4,430,381 A | 2/1984 | Harvey et al. |
| 4,460,490 A | 7/1984 | Barford et al. |
| 4,477,438 A | 10/1984 | Willcockson et al. |
| 4,478,683 A | 10/1984 | Orndorff |
| 4,501,681 A | 2/1985 | Groult et al. |
| 4,517,166 A | 5/1985 | Busacca |
| 4,521,375 A | 6/1985 | Houlsby |
| 4,529,534 A | 7/1985 | Richardson |
| 4,534,945 A | 8/1985 | Hopkins et al. |
| 4,536,313 A | 8/1985 | Hignett et al. |
| 4,545,917 A | 10/1985 | Smith et al. |
| 4,557,898 A | 12/1985 | Greene et al. |
| 4,557,935 A | 12/1985 | af Ekenstam et al. |
| 4,566,980 A | 1/1986 | Smith |
| 4,591,565 A | 5/1986 | Branner-Jorgensen et al. |
| 4,592,488 A | 6/1986 | Simon et al. |
| 4,594,175 A | 6/1986 | Copeland |
| 4,595,520 A | 6/1986 | Heile et al. |
| 4,613,452 A | 9/1986 | Sanderson |
| 4,618,444 A | 10/1986 | Hudson et al. |
| 4,624,713 A | 11/1986 | Morganson et al. |
| 4,647,458 A | 3/1987 | Ueno et al. |
| 4,655,781 A | 4/1987 | Sieh et al. |
| 4,659,494 A | 4/1987 | Soldanski et al. |
| 4,666,622 A | 5/1987 | Martin et al. |
| 4,671,891 A | 6/1987 | Hartman |
| 4,680,134 A | 7/1987 | Heile et al. |
| 4,681,914 A | 7/1987 | Olson et al. |
| 4,683,618 A | 8/1987 | O'Brien |
| 4,692,335 A | 9/1987 | Iwanski |
| 4,695,290 A | 9/1987 | Kindig et al. |
| 4,704,404 A | 11/1987 | Sanderson |
| 4,711,738 A | 12/1987 | Copeland |
| 4,715,980 A | 12/1987 | Lopes et al. |
| 4,731,195 A | 3/1988 | Olson |
| 4,732,694 A | 3/1988 | Gowland et al. |
| 4,738,840 A | 4/1988 | Simon et al. |
| 4,740,308 A | 4/1988 | Fremont et al. |
| 4,743,447 A | 5/1988 | Le Rouzic et al. |
| 4,753,033 A | 6/1988 | Kindig |
| 4,756,844 A | 7/1988 | Walles et al. |
| 4,762,637 A | 8/1988 | Aronson et al. |
| 4,772,290 A | 9/1988 | Mitchell et al. |
| 4,776,974 A | 10/1988 | Stanton et al. |
| 4,783,278 A | 11/1988 | Sanderson et al. |
| 4,793,942 A | 12/1988 | Lokkesmoe et al. |
| 4,802,994 A | 2/1989 | Mouche et al. |
| 4,824,591 A | 4/1989 | Dyroff et al. |
| 4,830,766 A | 5/1989 | Gallup et al. |
| 4,830,773 A | 5/1989 | Olson |
| 4,834,900 A | 5/1989 | Soldanski et al. |
| 4,846,993 A | 7/1989 | Lentsch et al. |
| 4,863,632 A | 9/1989 | Aronson et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorinez |
| 4,917,815 A | 4/1990 | Beilfuss et al. |
| 4,919,841 A | 4/1990 | Kamel et al. |
| 4,920,100 A | 4/1990 | Lehmann et al. |
| 4,923,677 A | 5/1990 | Simon et al. |
| 4,933,102 A | 6/1990 | Olson |
| 4,937,066 A | 6/1990 | Vlock |
| 4,943,414 A | 7/1990 | Jacobs et al. |
| 4,945,100 A | 7/1990 | Nyfeler et al. |
| 4,986,963 A | 1/1991 | Corcoran et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,013,560 A | 5/1991 | Stentz et al. |
| 5,015,408 A | 5/1991 | Reuss |
| 5,017,617 A | 5/1991 | Kihara et al. |
| 5,018,577 A | 5/1991 | Pardue et al. |
| 5,021,096 A | 6/1991 | Abadi |
| 5,023,000 A | 6/1991 | Kneller et al. |
| 5,030,240 A | 7/1991 | Wiersema et al. |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,085,794 A | 2/1992 | Kneller et al. |
| 5,093,140 A | 3/1992 | Watanabe |

(56) References Cited

U.S. PATENT DOCUMENTS

| | | |
|---|---|---|
| 5,114,178 A | 5/1992 | Baxter |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,152,933 A | 10/1992 | Holland |
| 5,168,655 A | 12/1992 | Davidson et al. |
| 5,176,899 A | 1/1993 | Montgomery |
| 5,184,471 A | 2/1993 | Losacco et al. |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |
| 5,246,620 A | 9/1993 | Gethoffer et al. |
| 5,266,587 A | 11/1993 | Sankey et al. |
| 5,268,003 A | 12/1993 | Coope et al. |
| 5,269,962 A | 12/1993 | Brodbeck et al. |
| 5,279,757 A | 1/1994 | Gethoffer et al. |
| 5,288,331 A | 2/1994 | Rings et al. |
| 5,292,447 A | 3/1994 | Venturello et al. |
| 5,306,350 A | 4/1994 | Hoy et al. |
| 5,314,687 A | 5/1994 | Oakes et al. |
| 5,320,805 A | 6/1994 | Kramer et al. |
| 5,330,769 A | 7/1994 | McKinzie et al. |
| 5,336,500 A | 8/1994 | Richter et al. |
| 5,344,652 A | 9/1994 | Hall, II et al. |
| 5,358,653 A | 10/1994 | Gladfelter et al. |
| 5,364,650 A | 11/1994 | Guthery |
| 5,368,867 A | 11/1994 | Da Silva et al. |
| 5,382,376 A | 1/1995 | Michael et al. |
| 5,385,680 A | 1/1995 | Didier et al. |
| 5,391,324 A | 2/1995 | Reinhardt et al. |
| 5,409,633 A | 4/1995 | Clements et al. |
| 5,409,713 A | 4/1995 | Lokkesmoe et al. |
| 5,419,908 A | 5/1995 | Richter et al. |
| 5,429,769 A | 7/1995 | Nicholson et al. |
| 5,435,808 A | 7/1995 | Holzhauer et al. |
| 5,436,008 A | 7/1995 | Richter et al. |
| 5,437,868 A | 8/1995 | Oakes et al. |
| 5,451,346 A | 9/1995 | Amou et al. |
| 5,454,982 A | 10/1995 | Murch et al. |
| 5,463,112 A | 10/1995 | Sankey et al. |
| 5,466,825 A | 11/1995 | Carr et al. |
| 5,481,084 A | 1/1996 | Patrick et al. |
| 5,489,434 A | 2/1996 | Oakes et al. |
| 5,489,706 A | 2/1996 | Revell |
| 5,494,588 A | 2/1996 | LaZonby |
| 5,501,814 A | 3/1996 | Engelskirchen et al. |
| 5,508,046 A | 4/1996 | Cosentino et al. |
| 5,512,309 A | 4/1996 | Bender et al. |
| 5,527,898 A | 6/1996 | Bauer et al. |
| 5,545,343 A | 8/1996 | Brougham et al. |
| 5,545,374 A | 8/1996 | French et al. |
| 5,567,444 A | 10/1996 | Hei et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,616,335 A | 4/1997 | Nicolle et al. |
| 5,616,616 A | 4/1997 | Hall, II et al. |
| 5,622,708 A | 4/1997 | Richter et al. |
| 5,624,634 A | 4/1997 | Brougham et al. |
| 5,632,676 A | 5/1997 | Kurschner et al. |
| 5,641,530 A | 6/1997 | Chen |
| 5,656,302 A | 8/1997 | Cosentino et al. |
| 5,658,467 A | 8/1997 | LaZonby et al. |
| 5,658,595 A | 8/1997 | Van Os |
| 5,674,538 A | 10/1997 | Lokkesmoe et al. |
| 5,674,828 A | 10/1997 | Knowlton et al. |
| 5,683,724 A | 11/1997 | Hei et al. |
| 5,686,401 A | 11/1997 | Willey et al. |
| 5,692,392 A | 12/1997 | Swier |
| 5,712,239 A | 1/1998 | Knowlton et al. |
| 5,718,910 A | 2/1998 | Oakes et al. |
| 5,720,983 A | 2/1998 | Malone |
| 5,725,678 A | 3/1998 | Cannon et al. |
| 5,741,767 A | 4/1998 | Nicholson et al. |
| 5,756,139 A | 5/1998 | Harvey et al. |
| 5,785,867 A | 7/1998 | LaZonby et al. |
| 5,840,343 A | 11/1998 | Hall, II et al. |
| 5,851,483 A | 12/1998 | Nicolle et al. |
| 5,866,005 A | 2/1999 | Desimone et al. |
| 5,891,392 A | 4/1999 | Monicello et al. |
| 5,900,256 A | 5/1999 | Scoville, Jr. et al. |
| 5,902,619 A | 5/1999 | Rubow et al. |
| 5,914,303 A | 6/1999 | Sankey et al. |
| 5,954,851 A | 9/1999 | Sakae |
| 5,958,864 A | 9/1999 | Artiga Gonzalez et al. |
| 5,968,539 A | 10/1999 | Beerse et al. |
| 5,968,881 A | 10/1999 | Haeggberg et al. |
| 5,977,053 A | 11/1999 | Groth et al. |
| 5,989,611 A | 11/1999 | Stemmler, Jr. et al. |
| 5,993,562 A | 11/1999 | Roclofs et al. |
| 5,998,358 A | 12/1999 | Herdt et al. |
| 6,008,405 A | 12/1999 | Gray et al. |
| 6,010,729 A | 1/2000 | Gutzmann et al. |
| 6,024,986 A | 2/2000 | Hei |
| 6,028,104 A | 2/2000 | Schmidt et al. |
| 6,033,705 A | 3/2000 | Isaacs |
| 6,039,992 A | 3/2000 | Compardre et al. |
| 6,049,002 A | 4/2000 | Mattila et al. |
| 6,071,356 A | 6/2000 | Olsen |
| 6,080,712 A | 6/2000 | Revell et al. |
| 6,096,226 A | 8/2000 | Fuchs et al. |
| 6,096,266 A | 8/2000 | Duroselle |
| 6,096,348 A | 8/2000 | Miner et al. |
| 6,103,286 A | 8/2000 | Gutzmann et al. |
| 6,111,963 A | 8/2000 | Thompson, III |
| 6,113,963 A | 9/2000 | Gutzmann et al. |
| 6,160,110 A | 12/2000 | Thomaides et al. |
| 6,165,483 A | 12/2000 | Hei et al. |
| 6,176,971 B1 | 1/2001 | Sun Yu et al. |
| 6,183,807 B1 | 2/2001 | Gutzmann et al. |
| 6,194,367 B1 | 2/2001 | Talley |
| 6,197,739 B1 | 3/2001 | Oakes et al. |
| 6,204,234 B1 | 3/2001 | Herbots et al. |
| 6,204,238 B1 | 3/2001 | Oftring et al. |
| 6,221,323 B1 | 4/2001 | Mizuno et al. |
| 6,238,685 B1 | 5/2001 | Hei et al. |
| 6,257,253 B1 | 7/2001 | Lentsch et al. |
| 6,262,013 B1 | 7/2001 | Smith et al. |
| 6,271,190 B1 | 8/2001 | Boskamp et al. |
| 6,274,542 B1 | 8/2001 | Carr et al. |
| 6,277,344 B1 | 8/2001 | Hei et al. |
| 6,302,968 B1 | 10/2001 | Baum et al. |
| 6,303,556 B1 | 10/2001 | Kott et al. |
| 6,306,252 B1 | 10/2001 | Ryham |
| 6,310,025 B1 | 10/2001 | Del Duca et al. |
| 6,326,032 B1 | 12/2001 | Richter et al. |
| 6,342,472 B1 | 1/2002 | Legel et al. |
| 6,380,145 B1 | 4/2002 | Herbots et al. |
| 6,395,703 B2 | 5/2002 | Scepanski |
| 6,417,151 B1 | 7/2002 | Grothus et al. |
| 6,423,868 B1 | 7/2002 | Carr et al. |
| 6,436,445 B1 | 8/2002 | Hei et al. |
| 6,451,746 B1 | 9/2002 | Moore et al. |
| 6,468,955 B1 | 10/2002 | Smets et al. |
| 6,472,199 B1 | 10/2002 | Monken |
| 6,479,454 B1 | 11/2002 | Smith et al. |
| 6,489,281 B1 | 12/2002 | Smith et al. |
| 6,492,316 B1 | 12/2002 | Herbots et al. |
| 6,495,357 B1 | 12/2002 | Fuglsang et al. |
| 6,506,737 B1 | 1/2003 | Hei et al. |
| 6,514,556 B2 | 2/2003 | Hilgren et al. |
| 6,534,075 B1 | 3/2003 | Hei et al. |
| 6,541,436 B1 | 4/2003 | Arvanitidou et al. |
| 6,545,047 B2 | 4/2003 | Gutzmann et al. |
| 6,548,467 B2 | 4/2003 | Baker et al. |
| 6,572,789 B1 | 6/2003 | Yang et al. |
| 6,589,565 B1 | 7/2003 | Richter et al. |
| 6,593,283 B2 | 7/2003 | Hei et al. |
| 6,619,051 B1 | 9/2003 | Kilawee et al. |
| 6,624,133 B1 | 9/2003 | McKenzi et al. |
| 6,627,593 B2 | 9/2003 | Hei et al. |

(56) References Cited

U.S. PATENT DOCUMENTS

| | | |
|---|---|---|
| 6,627,657 B1 | 9/2003 | Hilgren et al. |
| 6,630,439 B1 | 10/2003 | Norwood et al. |
| 6,635,286 B2 | 10/2003 | Hei et al. |
| 6,638,902 B2 | 10/2003 | Tarara et al. |
| 6,674,538 B2 | 1/2004 | Takahashi |
| 6,693,069 B2 | 2/2004 | Körber et al. |
| 6,703,357 B1 | 3/2004 | Maurer et al. |
| 6,718,991 B1 | 4/2004 | Breyer et al. |
| 6,783,767 B2 | 8/2004 | Shroot et al. |
| 6,808,729 B1 | 10/2004 | Roselle et al. |
| 6,828,294 B2 | 12/2004 | Kellar et al. |
| 6,855,328 B2 | 2/2005 | Hei et al. |
| 6,866,888 B2 | 3/2005 | Baker et al. |
| 6,897,193 B2 | 5/2005 | Kischkel et al. |
| 6,903,064 B1 | 6/2005 | Kasturi et al. |
| 6,962,714 B2 | 11/2005 | Hei et al. |
| 6,964,787 B2 | 11/2005 | Swart et al. |
| 6,964,943 B1 | 11/2005 | Bettiol et al. |
| 6,982,241 B2 | 1/2006 | Smith et al. |
| 7,008,913 B2 | 3/2006 | Hei et al. |
| 7,056,536 B2 | 6/2006 | Richter et al. |
| 7,060,301 B2 | 6/2006 | Wei et al. |
| 7,074,749 B2 | 7/2006 | Tropsch et al. |
| 7,129,076 B2 | 10/2006 | Poulose et al. |
| 7,141,125 B2 | 11/2006 | McKechnie et al. |
| 7,150,884 B1 | 12/2006 | Hilgren et al. |
| 7,153,817 B2 | 12/2006 | Binder |
| 7,179,778 B2 | 2/2007 | Weber |
| 7,226,898 B2 | 6/2007 | Bragulla |
| 7,250,159 B1 | 7/2007 | Arnaud |
| 7,320,887 B2 | 1/2008 | Kottwitz et al. |
| 7,323,438 B2 | 1/2008 | Hedges et al. |
| 7,438,767 B2 | 10/2008 | McKechnie et al. |
| 7,448,556 B2 | 11/2008 | Muehlhausen et al. |
| 7,462,375 B2 | 12/2008 | Ge |
| 7,470,655 B2 | 12/2008 | Biering et al. |
| 7,498,051 B2 | 3/2009 | Man et al. |
| 7,501,388 B2 | 3/2009 | McClung |
| 7,504,123 B2 | 3/2009 | Man et al. |
| 7,504,124 B2 | 3/2009 | Man et al. |
| 7,507,429 B2 | 3/2009 | Man et al. |
| 7,510,859 B2 | 3/2009 | Wieland et al. |
| 7,517,847 B2 | 4/2009 | Catalfamo et al. |
| 7,611,882 B2 | 11/2009 | Bjornvad et al. |
| 7,659,354 B2 | 2/2010 | Song et al. |
| 7,682,403 B2 | 3/2010 | Gohl et al. |
| 7,727,946 B2 | 6/2010 | Catalfamo et al. |
| 7,749,334 B2 | 7/2010 | Biering et al. |
| 7,754,670 B2 | 7/2010 | Lange et al. |
| 7,754,671 B2 | 7/2010 | Lin et al. |
| 7,816,555 B2 | 10/2010 | Smith et al. |
| 7,887,641 B2 | 2/2011 | Man et al. |
| 7,892,536 B2 | 2/2011 | Kelemen et al. |
| 7,910,647 B2 | 3/2011 | Weide et al. |
| 7,915,212 B2 | 3/2011 | Yeung et al. |
| 7,928,049 B2 | 4/2011 | Wagner et al. |
| 7,939,485 B2 | 5/2011 | Price et al. |
| 7,985,570 B2 | 7/2011 | Wieland et al. |
| 7,994,251 B2 | 8/2011 | Rogmann et al. |
| 8,012,267 B2 | 9/2011 | Jekel et al. |
| 8,022,027 B2 | 9/2011 | Souter et al. |
| 8,043,650 B2 | 10/2011 | Gutzmann et al. |
| 8,058,374 B2 | 11/2011 | Rodrigues et al. |
| 8,063,008 B2 | 11/2011 | Dicosimo et al. |
| 8,119,588 B2 | 2/2012 | Bernhardt et al. |
| 8,124,132 B2 | 2/2012 | Hilgren et al. |
| 8,178,352 B2 | 5/2012 | Tokhtuev et al. |
| 8,202,830 B2 | 6/2012 | Miralles et al. |
| 8,222,196 B2 | 7/2012 | Smith et al. |
| 8,246,906 B2 | 8/2012 | Hei et al. |
| 8,247,363 B2 | 8/2012 | Fernholz et al. |
| 8,748,365 B2 | 6/2014 | Olson et al. |
| 8,784,790 B2 | 7/2014 | Myntti et al. |
| 8,871,699 B2 | 10/2014 | Silvernail et al. |
| 8,940,676 B2 | 1/2015 | Catlin et al. |
| 8,999,399 B2 | 4/2015 | Lisowsky et al. |
| 9,018,142 B2 | 4/2015 | Rovison, Jr. et al. |
| 9,023,784 B2 | 5/2015 | Silvernail et al. |
| 9,051,285 B2 | 6/2015 | Rohwer et al. |
| 9,255,242 B2 | 2/2016 | Olson et al. |
| 9,670,434 B2 | 6/2017 | Silvernail et al. |
| 9,752,105 B2 | 9/2017 | Stokes et al. |
| 9,994,799 B2 | 6/2018 | Silvernail et al. |
| 10,349,852 B2 | 7/2019 | Saumarez |
| 10,358,622 B2 * | 7/2019 | Stokes .................. C11D 3/365 |
| 10,377,971 B2 | 8/2019 | Silvernail et al. |
| 11,001,784 B2 | 5/2021 | Silvernail et al. |
| 11,053,458 B2 | 7/2021 | Silvernail et al. |
| 2002/0013252 A1 | 1/2002 | Schmiedel et al. |
| 2002/0037824 A1 | 3/2002 | Smets |
| 2002/0082181 A1 | 6/2002 | Humphrey et al. |
| 2002/0086903 A1 | 7/2002 | Giambrone et al. |
| 2002/0128312 A1 | 9/2002 | Hei et al. |
| 2002/0159917 A1 | 10/2002 | Swart et al. |
| 2002/0160930 A1 | 10/2002 | Emmerson et al. |
| 2002/0177220 A1 | 11/2002 | Monken |
| 2002/0192340 A1 | 12/2002 | Swart et al. |
| 2003/0087786 A1 | 5/2003 | Hei et al. |
| 2003/0139310 A1 | 7/2003 | Smith et al. |
| 2003/0139311 A1 | 7/2003 | Biering et al. |
| 2003/0157192 A1 | 8/2003 | Shroot et al. |
| 2003/0166484 A1 | 9/2003 | Kingma et al. |
| 2003/0191040 A1 | 10/2003 | Adriaanse et al. |
| 2003/0194433 A1 | 10/2003 | Hei et al. |
| 2003/0199583 A1 | 10/2003 | Gutzmann et al. |
| 2004/0007255 A1 | 1/2004 | Labib et al. |
| 2004/0029755 A1 | 2/2004 | Bragulla |
| 2004/0146426 A1 | 7/2004 | Biering et al. |
| 2004/0147423 A1 | 7/2004 | Scialla et al. |
| 2004/0194810 A1 | 10/2004 | Strothoff et al. |
| 2004/0259755 A1 | 12/2004 | Orlich et al. |
| 2004/0266639 A1 | 12/2004 | Spindler |
| 2005/0003979 A1 | 1/2005 | Lentsch et al. |
| 2005/0020464 A1 | 1/2005 | Smith et al. |
| 2005/0086757 A1 | 4/2005 | Lann |
| 2005/0137105 A1 | 6/2005 | Griese et al. |
| 2005/0137107 A1 | 6/2005 | Griese et al. |
| 2005/0153859 A1 | 7/2005 | Gohl et al. |
| 2005/0183744 A1 | 8/2005 | Staub et al. |
| 2005/0245411 A1 | 11/2005 | Yang et al. |
| 2005/0282261 A1 | 12/2005 | Sauter et al. |
| 2006/0003028 A1 | 1/2006 | Myers et al. |
| 2006/0042665 A1 | 3/2006 | Fernholz |
| 2006/0046945 A1 | 3/2006 | Herdt et al. |
| 2006/0069003 A1 | 3/2006 | Song et al. |
| 2006/0069004 A1 | 3/2006 | Song et al. |
| 2006/0113506 A1 | 6/2006 | Man et al. |
| 2006/0118141 A1 | 6/2006 | Andriola et al. |
| 2006/0122090 A1 | 6/2006 | Spanier et al. |
| 2006/0134239 A1 | 6/2006 | Weide et al. |
| 2006/0247144 A1 | 11/2006 | Geret |
| 2006/0257498 A1 | 11/2006 | Stingl et al. |
| 2006/0270580 A1 | 11/2006 | Smith et al. |
| 2007/0020364 A1 | 1/2007 | Burnett et al. |
| 2007/0084650 A1 | 4/2007 | Schwei et al. |
| 2007/0102030 A1 | 5/2007 | Young |
| 2007/0128129 A1 | 6/2007 | Stehr et al. |
| 2007/0155835 A1 | 7/2007 | Weide et al. |
| 2007/0173428 A1 | 7/2007 | Appleby et al. |
| 2007/0190177 A1 | 8/2007 | Kling et al. |
| 2008/0014284 A1 | 1/2008 | Meyer et al. |
| 2008/0026026 A1 | 1/2008 | Lu et al. |
| 2008/0076692 A1 | 3/2008 | Carvell et al. |
| 2008/0118580 A1 | 5/2008 | Bockmuhl et al. |
| 2008/0121250 A1 | 5/2008 | Fernholz et al. |
| 2008/0261851 A1 | 10/2008 | Barthel et al. |
| 2008/0263778 A1 | 10/2008 | Baars et al. |
| 2008/0271760 A1 | 11/2008 | Housmekerides et al. |
| 2008/0274930 A1 | 11/2008 | Smith et al. |
| 2009/0061017 A1 | 3/2009 | Pedersen et al. |
| 2009/0101587 A1 | 4/2009 | Blokker et al. |
| 2009/0145859 A1 | 6/2009 | Man et al. |
| 2009/0288683 A1 | 11/2009 | Cummings et al. |
| 2009/0325841 A1 | 12/2009 | Erickson et al. |

(56) References Cited

U.S. PATENT DOCUMENTS

| | | |
|---|---|---|
| 2010/0021558 A1 | 1/2010 | Dada et al. |
| 2010/0075883 A1 | 3/2010 | Geret et al. |
| 2010/0093587 A1 | 4/2010 | Preuschen et al. |
| 2010/0144958 A1 | 6/2010 | Findlay et al. |
| 2010/0160449 A1 | 6/2010 | Rovison, Jr. et al. |
| 2010/0189707 A1 | 7/2010 | Barnett |
| 2010/0300044 A1 | 12/2010 | Man et al. |
| 2010/0330013 A1 | 12/2010 | O'Connell et al. |
| 2011/0165261 A1 | 7/2011 | Derby et al. |
| 2011/0177146 A1 | 7/2011 | Cahill et al. |
| 2011/0182771 A1 | 7/2011 | Kany et al. |
| 2011/0182959 A1 | 7/2011 | Cahill et al. |
| 2011/0308553 A1 | 12/2011 | Strothoff et al. |
| 2012/0046216 A1 | 2/2012 | Hodge et al. |
| 2012/0121679 A1 | 5/2012 | Cannon et al. |
| 2012/0128614 A1 | 5/2012 | Rieth et al. |
| 2012/0148751 A1 | 6/2012 | Herdt et al. |
| 2012/0165237 A1 | 6/2012 | Silvernail |
| 2012/0208734 A1 | 8/2012 | Eiting et al. |
| 2012/0291820 A1 | 11/2012 | Strothoff et al. |
| 2021/0363467 A1 | 11/2021 | Silvernail et al. |

FOREIGN PATENT DOCUMENTS

| | | |
|---|---|---|
| CA | 2122136 A1 | 4/1993 |
| CA | 2163757 C | 12/1994 |
| CA | 2314648 A1 | 1/2001 |
| CA | 2314660 A1 | 1/2001 |
| CA | 2448548 A1 | 12/2002 |
| CA | 2450893 A1 | 1/2003 |
| CA | 2531098 A1 | 1/2005 |
| CA | 2567210 A1 | 2/2006 |
| CN | 101228192 B | 5/2011 |
| CN | 102844125 A | 12/2012 |
| DE | 4324202 A1 | 12/1994 |
| DE | 19639603 A1 | 9/1996 |
| DE | 19754290 A1 | 6/1999 |
| DE | 19906660 A1 | 1/2000 |
| DE | 19949980 A1 | 4/2001 |
| DE | 10127919 A1 | 12/2002 |
| EP | 0096566 A1 | 12/1983 |
| EP | 0133354 A1 | 2/1985 |
| EP | 0256148 A1 | 2/1988 |
| EP | 0383214 A1 | 8/1990 |
| EP | 0511081 A1 | 10/1992 |
| EP | 0511091 A1 | 10/1992 |
| EP | 0609273 A1 | 8/1994 |
| EP | 0612843 | 8/1994 |
| EP | 0658594 B1 | 6/1995 |
| EP | 0691398 A1 | 1/1996 |
| EP | 0976867 B1 | 2/2000 |
| EP | 1063281 A2 | 12/2000 |
| EP | 1065261 A2 | 1/2001 |
| EP | 1127939 A1 | 8/2001 |
| EP | 1138335 A1 | 10/2001 |
| EP | 1260234 A1 | 11/2002 |
| EP | 1293215 A1 | 3/2003 |
| EP | 1302108 A2 | 4/2003 |
| EP | 1451243 B9 | 9/2004 |
| EP | 1477552 A1 | 11/2004 |
| GB | 1148046 | 4/1969 |
| GB | 1351977 | 5/1974 |
| GB | 1571357 | 7/1980 |
| GB | 2427614 | 1/2007 |
| IN | 226322 | 3/2005 |
| IN | 212385 | 4/2005 |
| IN | 200300222 | 4/2005 |
| IN | 200000442 | 4/2007 |
| IN | 200502145 | 8/2007 |
| IN | 200902559 | 12/2009 |
| IN | 201205604 | 3/2014 |
| IN | 201301987 | 9/2014 |
| IN | 201211025 | 10/2014 |
| IN | 201401913 | 3/2015 |
| IN | 201402010 | 3/2015 |
| JP | 60228683 A | 11/1985 |
| JP | 6112878 A | 1/1986 |
| JP | 7330994 A | 12/1995 |
| JP | 1150096 A | 2/1999 |
| JP | 1161177 A | 3/1999 |
| JP | 1161178 A | 3/1999 |
| JP | 1161179 A | 3/1999 |
| JP | 1161180 A | 3/1999 |
| JP | 1161181 A | 3/1999 |
| JP | 1161183 A | 3/1999 |
| JP | 1161185 A | 3/1999 |
| JP | 3370571 B2 | 11/2002 |
| JP | 4851093 B2 | 3/2006 |
| JP | 2007246432 A | 9/2007 |
| JP | 5036962 B2 | 9/2012 |
| JP | 2013129808 A | 7/2013 |
| JP | 2013158743 A | 8/2013 |
| KR | 20060046896 A | 5/2006 |
| KR | 20080099255 A | 11/2008 |
| MX | 2012008140 A | 8/2012 |
| WO | 199007501 A1 | 7/1990 |
| WO | 9202309 A1 | 2/1992 |
| WO | 9407982 A1 | 4/1994 |
| WO | 199418299 A1 | 8/1994 |
| WO | 9423000 A1 | 10/1994 |
| WO | 199521290 A1 | 8/1995 |
| WO | 9526392 A1 | 10/1995 |
| WO | 9526393 A1 | 10/1995 |
| WO | 9617920 A1 | 6/1996 |
| WO | 9722651 | 6/1997 |
| WO | 199722651 A1 | 6/1997 |
| WO | 9731999 A1 | 9/1997 |
| WO | 9805749 A1 | 2/1998 |
| WO | 9815607 | 4/1998 |
| WO | 9815608 | 4/1998 |
| WO | 9856760 A1 | 12/1998 |
| WO | 9903962 A1 | 1/1999 |
| WO | 9910466 A1 | 3/1999 |
| WO | 9914304 A1 | 3/1999 |
| WO | 9919449 A1 | 4/1999 |
| WO | 199920726 A1 | 4/1999 |
| WO | 9941350 A1 | 8/1999 |
| WO | 9941351 A1 | 8/1999 |
| WO | 0037041 | 6/2000 |
| WO | 0060042 A1 | 10/2000 |
| WO | 0061715 A1 | 10/2000 |
| WO | 0071651 A2 | 11/2000 |
| WO | 0102528 A1 | 1/2001 |
| WO | 0102529 A1 | 1/2001 |
| WO | 0107551 A1 | 2/2001 |
| WO | 0107560 A1 | 2/2001 |
| WO | 0136579 A1 | 5/2001 |
| WO | 0138471 A1 | 5/2001 |
| WO | 0146358 A2 | 6/2001 |
| WO | 0176442 | 10/2001 |
| WO | 0202725 | 1/2002 |
| WO | 03004408 | 1/2003 |
| WO | 03048291 A1 | 6/2003 |
| WO | 03073849 A1 | 9/2003 |
| WO | 2004091557 | 10/2004 |
| WO | 06105863 A1 | 10/2006 |
| WO | 06108490 A1 | 10/2006 |
| WO | 07025603 A1 | 3/2007 |
| WO | 2008028896 | 3/2008 |
| WO | 2008035071 | 3/2008 |
| WO | 2009112992 A1 | 9/2009 |
| WO | 09122125 A1 | 10/2009 |
| WO | 2010000636 | 1/2010 |
| WO | 2010033746 | 3/2010 |
| WO | 2010033747 | 3/2010 |
| WO | 10146543 A1 | 12/2010 |
| WO | 2011014783 | 2/2011 |
| WO | 2011024094 | 3/2011 |
| WO | 11070392 A1 | 6/2011 |
| WO | 2011089493 | 7/2011 |
| WO | 2011161459 | 12/2011 |
| WO | 12014016 A1 | 2/2012 |
| WO | 12028196 A1 | 3/2012 |
| WO | 12036702 A1 | 3/2012 |

(56) References Cited

FOREIGN PATENT DOCUMENTS

| WO | 2012028203 A1 | 3/2012 |
| WO | 2012042000 A1 | 4/2012 |
| WO | 12128629 A1 | 9/2012 |
| WO | 2012155986 A1 | 11/2012 |
| WO | 2012156369 A1 | 11/2012 |

OTHER PUBLICATIONS

Sasol, "Specialty Ethoxylates based on short chain alcohols", Sasol Performance Chemicals booklet, 20 pages, Sep. 9, 2015.

European Patent Office, "Extended European Search Report", issued in connection to Application No. 14784618.2, dated Sep. 5, 2016, 8 pages.

CN101228192—Kraton Polymers—English Translation May 25, 2011.

CN102844125—Ecolab USA Inc.—English Translation Dec. 26, 2012.

DE4324202—Henkel Ecolab GMBH & Co.—English Translation Dec. 1, 1994.

DE10127919—Ecolab GMBH & Co.—English Translation Dec. 19, 2002.

DE19906660—Haka Kunz GmbH—English Translation Jan. 27, 2000.

DE19949980—Henkel KGaA—English Translation Apr. 19, 2001.

EP0256148—Jon A. Benckiser—English Translation Feb. 24, 1988.

EP0511081—Roquette Freres—English Translation Oct. 28, 1992.

EP0609273—Henkel Kommanditgesellschaft—English Translation Aug. 10, 1994.

EP0658594—Witco Vinyl Additives GmbH—English Translation Jun. 21, 1995.

EP1451243—Roquette Freres—English Translation Sep. 1, 2004.

JP4851093—Novo Enzyme Akuti Angeles Cub Graphics13 English Translation Mar. 23, 2006.

JP7330994—Nippon Synthetic Chemical Industry—English Translation Dec. 19, 1995.

JPS60228683—Mitsubishi Electric—English Translation Nov. 13, 1985.

JPS6112878—Mitsubishi Electric—English Translation Jan. 21, 1986.

WO 94/07982—Henkel Kommanditgesellschaft—English Translation Apr. 14, 1994.

WO 01/46358—Henkel Kommanditgesellschaft—English Translation Jun. 28, 2001.

Ecolab USA Inc., PCT/US2014/034011, "Notification of Transmittal of The International Search report and The Written Opinion of The International Searching Authority, or The Declaration" dated Aug. 11, 2014.

\* cited by examiner

PEROXYCARBOXYLIC ACID BASED SANITIZING RINSE ADDITIVES FOR USE IN WARE WASHING

CROSS REFERENCE TO RELATED APPLICATION

This is a Continuation Application of U.S. Ser. No. 13/863,001, filed Apr. 15, 2013, which is herein incorporated by reference in its entirety.

FIELD OF THE INVENTION

The present invention relates to a concentrated liquid sanitizing and rinse composition. In particular, peroxycarboxylic acid sanitizing and rinsing compositions and methods for using the compositions are disclosed. The sanitizing and rinsing compositions are formulated in a single liquid concentrate, replacing a traditional dual product of a sanitizer and rinse aid. The single dual use formulation provides a sanitizing peroxycarboxylic acid and a rinse aid surfactant(s) compatible with the sanitizing agent. Methods of using the single dual use formulations can include in aqueous solutions on articles including, for example, cookware, dishware, flatware, glasses, cups, hard surfaces, glass surfaces, etc. Surprising, certain embodiments of the sanitizing rinse aid compositions are effective at essentially neutral pHs against gram negative organisms at elevated temperatures.

BACKGROUND OF THE INVENTION

Mechanical warewashing machines including dishwashers have been common in the institutional and household environments for many years. Such automatic warewashing machines clean dishes using two or more cycles which can include initially a wash cycle followed by a rinse cycle. Such automatic warewashing machines can also utilize other cycles, for example, a soak cycle, a pre-wash cycle, a scrape cycle, additional wash cycles, additional rinse cycles, a sanitizing cycle, and/or a drying cycle. Any of these cycles can be repeated, if desired and additional cycles can be used. Detergents and/or sanitizers are conventionally used in these warewashing applications to provide cleaning, disinfecting and/or sanitizing. Dishmachines can remove soil by using a combination of various detergents and/or sanitizers, temperatures, and/or mechanical action from water. In some aspects where a sanitizer is not employed, water is heated to provide sanitization of the ware, placing an increase utility demand on a ware wash machine.

In addition to detergents and sanitizers, rinse aids are also conventionally used in warewashing applications to promote drying and to prevent the formation of spots on the ware being washed. In order to reduce the formation of spotting, rinse aids have commonly been added to water to form an aqueous rinse that is sprayed on the ware after cleaning is complete. A number of rinse aids are currently known, each having certain advantages and disadvantages, such as those disclosed in U.S. Pat. Nos. 3,592,774, 3,625,901, 3,941,713, 4,005,024, 4,187,121, 4,147,559, 4,624,713. In addition, further disclosure of rinse additives including nonionic surfactants is disclosed in Schick, "Nonionic Surfactants", published by Marcel Dekker, and John L. Wilson, Soap and Chemical Specialties, February 1958, pp. 48-52 and 170-171, which is herein incorporated by reference in its entirety.

There remains an ongoing need for alternative rinse aid compositions. There further remains an ongoing need for improved efficacy of dishmachines, including maximizing the efficacy of the combination of detergents, sanitizers and/or rinse aids formulations. In addition, there is a desire among consumers, both institutional and household, to reduce the utilities required for operating such dishmachines. It is against this background that the present disclosure is made to develop a combination sanitizing agent and rinse aid into a single, stable formulation.

Accordingly, it is an objective of the claimed invention to develop concentrated liquid compositions and methods of using the same for warewashing applications to provide desired cleaning and rinsing performance in a single, dual use formulation that minimizes utilities consumed by such applications to that equivalent to low temperature warewashing applications.

A further object of the invention is to provide a non-chlorine based sanitizing system for warewashing and other applications containing peroxycarboxylic acids with non-foaming rinse additives.

A further object of the invention is to provide warewashing applications that reduce energy consumption required for warewashing methods similar to the energy consumption of low temperature machines.

A still further object of the invention is to provide a single dual formulation for both sanitizing and rinsing, thereby reducing the overall chemistry consumption of the application of use.

Other objects, advantages and features of the present invention will become apparent from the following specification taken in conjunction with the accompanying drawings.

BRIEF SUMMARY OF THE INVENTION

An advantage of the invention is the combination of a peroxycarboxylic acid sanitizer chemistry with compatible rinse aid surfactants into a single, stable liquid concentrate. Beneficially, according to the embodiments of the invention, the liquid concentrate provides a single dual use formulation to replace conventional sanitizing and rinse aid formulations provided in separate products. As a result, the claimed compositions and methods of using the compositions result in significant benefits, including: a decrease in utilities (e.g., energy and water) that is expected from low temperature door dishwashing machines; concentrated multi-part compositions including the sanitizing agent, rinse additives and optional additional components in a dual use composition; and enables use of lower voltage and amperage dishmachine due to use of the peroxycarboxylic acid sanitizing agents.

In an embodiment, the present invention discloses a sanitizing rinse additive composition comprising: a C1-C22 peroxycarboxylic acid; a C1-C22 carboxylic acid; hydrogen peroxide; and a nonionic defoaming and wetting surfactant(s). In an aspect of the invention, the composition is a low odor peroxycarboxylic acid composition. In a further aspect of the invention, the composition when diluted from about 0.01% weight/volume to about 1% weight/volume provides at least a 5 log reduction in pathogenic organisms at a temperature of at least about 100° F.

In a further embodiment, the present invention discloses a sanitizing rinse additive composition comprising: from about 1 wt-% to about 40 wt-% C1-C22 peroxycarboxylic acid; from about 1 wt-% to about 80 wt-% C1-C22 carboxylic acid; from about 1 wt-% to about 80 wt-% hydrogen peroxide; from about 1 wt-% to about 25 wt-% alkyl-ethylene oxide-propylene oxide type nonionic surfactant; and from about 1 wt-% to about 20 wt-% alcohol ethoxylate nonionic surfactant. In an aspect of the invention, the composition is a low odor, liquid concentrate. In a further aspect, the use solution of the liquid concentrate has a pH greater than about 5. In a further aspect, the composition when diluted from about weight/volume to about 0.02% weight/volume provides at least a 5 log reduction in pathogenic organisms at a temperature of at least about 100° F.

In a still further embodiment, the present invention discloses a method of sanitizing and rinsing comprising: providing a low odor, liquid concentrate, equilibrium peroxycarboxylic acid sanitizing rinse aid composition, wherein the composition comprises: a $C_1$-$C_{22}$ peroxycarboxylic acid; a $C_1$-$C_{22}$ carboxylic acid; hydrogen peroxide; an alkyl-ethylene oxide-propylene oxide type nonionic surfactant; and an alcohol ethoxylate nonionic surfactant; and sanitizing a surface in need thereof without an additional rinsing step. In a further aspect, the composition when diluted from about 0.01% weight/volume to about 1% weight/volume provides at least a 5 log reduction in pathogenic organisms at a temperature of at least about 100° F.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
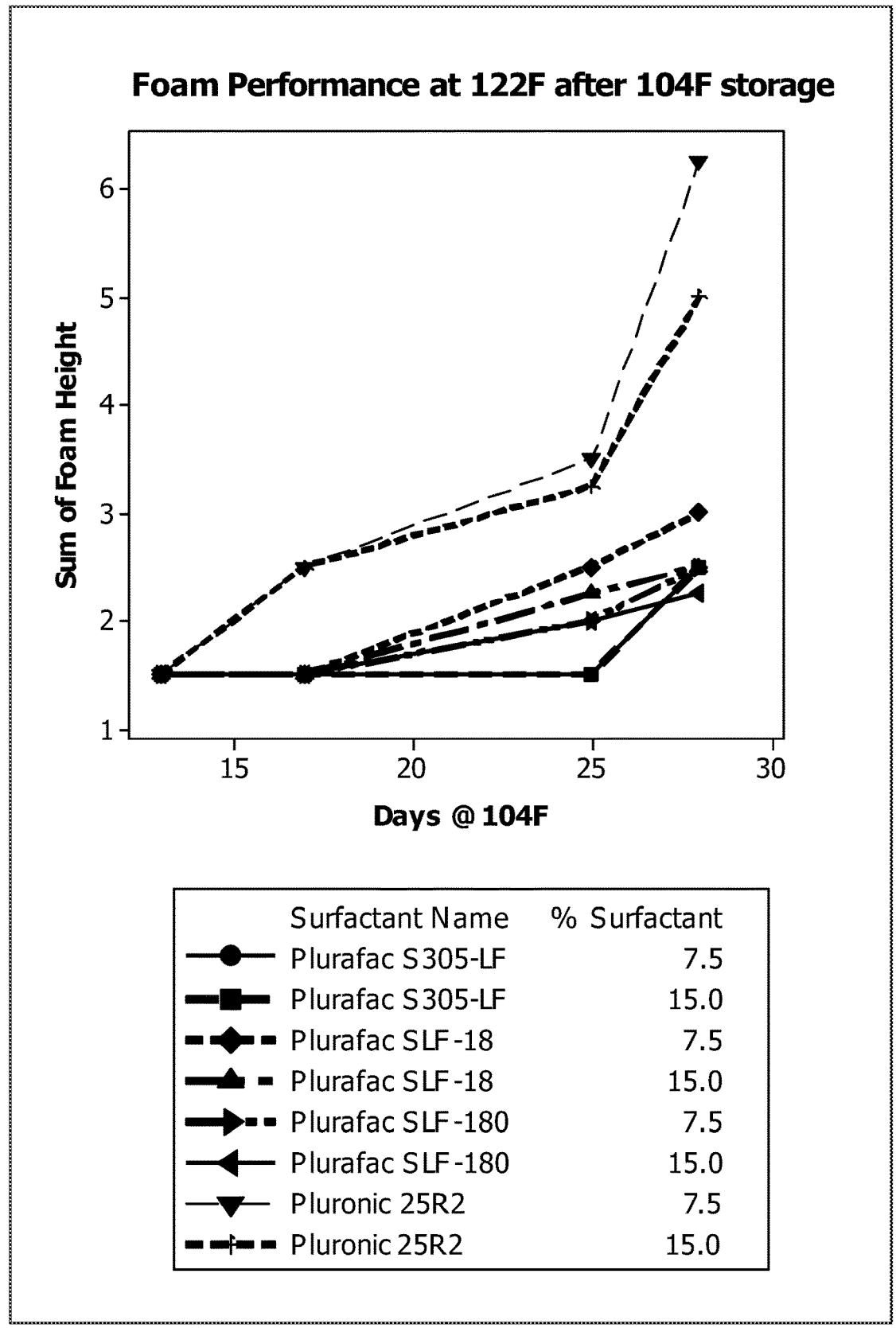
FIG. 1 shows foam performance at 122° F. after storage at 104° F. using the various surfactants combinations according to embodiments of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular sanitizing and rinsing compositions and methods of employing the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

An "antiredeposition agent" refers to a compound that helps keep suspended in water instead of redepositing onto the object being cleaned. Antiredeposition agents are useful in the present invention to assist in reducing redepositing of the removed soil onto the surface being cleaned.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A. C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention.

These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, buns, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

As used herein, the term "phosphorus-free" or "substantially phosphorus-free" refers to a composition, mixture, or ingredient that does not contain phosphorus or a phosphorus-containing compound or to which phosphorus or a phosphorus-containing compound has not been added. Should phosphorus or a phosphorus-containing compound be present through contamination of a phosphorus-free composition, mixture, or ingredients, the amount of phosphorus shall be less than 0.5 wt %. More preferably, the amount of phosphorus is less than 0.1 wt-%, and most preferably the amount of phosphorus is less than 0.01 wt % in phosphorus-free compositions.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms. According to other aspects of the invention, a sanitizer provides a 99.999% reduction (5-log order reduction) at a temperature of at least about 100° F. against several test organisms, including gram negative organisms.

As used herein, the term "soil" or "stain" refers to a non-polar oily substance which may or may not contain particulate matter such as mineral clays, sand, natural mineral matter, carbon black, graphite, kaolin, environmental dust, etc.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "substantially similar cleaning performance" refers generally to achievement by a substitute cleaning, sanitizing and/or rinsing product or substitute cleaning, sanitizing and/or rinsing system of generally the same degree (or at least not a significantly lesser degree) of cleanliness or with generally the same expenditure (or at least not a significantly lesser expenditure) of effort, or both.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Compositions

While an understanding of the mechanism is not necessary to practice the present invention and while the present invention is not limited to any particular mechanism of action, it is contemplated that, in some embodiments, equilibrium peroxycarboxylic acid compositions are formulated with compatible non-foaming rinse additives (i.e. surfactants) to provide approximately neutral pH sanitizing and rinsing compositions with suitable stability. Beneficially, the formulations according to the present invention allow a single dual formulation of the concentrated equilibrium peroxycarboxylic acid compositions with the rinse aid surfactants to allow a single formulation (i.e. one part system) instead of the separate products for cleaning, sanitizing and/or rinsing which are customarily used in warewashing and other cleaning and/or sanitizing applications.

It is unexpected according to the invention, that the single formulation is able to effectively replace two or three distinct formulations (e.g. detergent, sanitizer and rinse additive) while providing the desired technical effect. These results were unexpected as one skilled in the art does not expect a low-foaming or non-foaming rinse additive or surfactant(s) to be compatible with peroxycarboxylic acids and hydrogen peroxide. This expected incompatibility is similar to the understanding in the art that nonionic surfactants are also incompatible with chlorine bleach-based sanitizing compositions. One skilled in the art expects the bleach and/or peracid to degrade the nonionic surfactants. Therefore, it is unexpected and highly beneficial, according to the invention, that the particular non-foaming rinse additives are formulated into a stable, concentrated peroxycarboxylic acid composition.

In an embodiment, the present composition exhibits advantageous stability of the peroxycarboxylic acid. In an aspect of the invention, the concentrated compositions have shelf-stability of one year at room temperature, as confirmed by accelerated shelf-life and stability testing. In an aspect, stability refers to the amount of peroxycarboxylic acid in the compositions remaining at about 80% or more, about 85% or more, about 90% or more, or about 95% or more of the initial values or use composition levels.

It is further unexpected that the compositions provide at least substantially similar rinsing performance to those rinse aids or surfactants formulated into two or more part systems. According to the invention, the one part system provides sanitizing and sufficient rinse aid performance, including sheeting (i.e. chemical species causes the aqueous rinse to sheet from a treated surface such as a ware), spot-free ware and quick drying performance, in the presence of peroxycarboxylic acid and hydrogen peroxide. As a further unexpected benefit, the combination sanitizing and rinse aid formulations reduce and/or do not exceed the cost to consumers in comparison to such conventional two or three part formulations for warewashing applications.

In an aspect, the single use, dual compositions include concentrated equilibrium compositions comprising peroxycarboxylic acid(s), hydrogen peroxide, corresponding carboxylic acid(s), a solvent, e.g., water, rinse aid surfactants, and other optional additional functional ingredients. In an aspect, the concentrated, equilibrium liquid compositions include the exemplary ranges shown in Table 1.

TABLE 1

| Material | First Exemplary Range wt-% | Second Exemplary Range wt-% | Third Exemplary Range wt-% |
| --- | --- | --- | --- |
| Solvent (e.g. Water) | 0-80 | 0.001-60 | 0.01-50 |
| Peroxycarboxylic Acid | 0.1-40 | 1-20 | 1-10 |
| Carboxylic Acid | 0.1-80 | 1-40 | 1-15 |
| Hydrogen Peroxide | 1-75 | 1-50 | 1-25 |
| Rinse Aid Surfactants (defoaming and wetting surfactants) | 1-50 | 1-25 | 10-25 |
| Additional Functional Ingredients (e.g. stabilizing agent(s), additional surfactants, coupling agents) | 0-50 | 1-50 | 10-50 |

Embodiments of the Concentrate Compositions

According to the invention, the concentrated, equilibrium compositions set forth in Table 1 have acidic pHs, such as from about 0 to about 4. However, according to aspects of the invention, the diluted use solutions may have acidic or neutral to alkaline pH depending upon a particular application of use thereof. In one aspect, the pH of the use solution of the compositions is between about 0 to about 4. In a further aspect, the pH of the use solution of the compositions is between about 5 to about 9, preferably from about 5.5 to about 8.5. Without limiting the scope of invention, the numeric ranges are inclusive of the numbers defining the range and include each integer within the defined range.

In additional aspects, the concentrated, equilibrium compositions set forth in Table 1 are suitable for dilution and use at temperatures up to about 100° F., up to about 110° F., up to about 120° F., up to about 180° F., at temperatures from about 100° F. to about 140° F., at temperatures above about 140° F., and at temperatures up to or above 180° F. Without limiting the scope of invention, the numeric ranges are inclusive of the numbers defining the range and include each integer within the defined range.

It is unexpected according to certain embodiments of the compositions and methods of the invention that the use solutions of neutral to alkaline pH (e.g. about 5-9) provide micro efficacy against pathogenic organisms, including for example gram negative organisms important for food safety sanitizing applications. This is unexpected as a neutral pH POOA sanitizing composition was expected to have ineffective antimicrobial efficacy against *E. coli* or other gram negative organisms even at elevated temperatures (e.g., 100° F.-140° F., such as those temperatures currently required for chemical sanitization with bleach in ware wash machines). This is evident by the use of peroxycarboxylic acids, such as the medium length alkyl chain peracid in use solutions having acidic pH (generally pH of less than <4.0) to provide sufficient sanitizing efficacy against gram negative organisms, such as *E. coli*.

In additional aspects, the concentrated, equilibrium compositions set forth in Table 1 are low odor products. In preferred aspects, the concentrated equilibrium compositions include less than about 2 wt-% peroxyacetic acid, or preferably exclude peroxyacetic acid. In other aspects, the concentrated, equilibrium compositions contain short chain carboxylic acids (and corresponding peroxycarboxylic acids) at a level insufficient to cause odor offensive to a typical person. In certain embodiments, the present concentrated compositions include, for example, less than 10 wt-%, less than less than 5 wt-%, less than 2 wt-%, or less than 1 wt-% acetic acid or other malodor-causing short chain carboxylic acids.

The sanitizing rinse aid compositions may include concentrate compositions or may be diluted to form use compositions. In general, a concentrate refers to a composition that is intended to be diluted with water to provide a use solution that contacts an object to provide the desired cleaning, rinsing, or the like. The sanitizing rinse aid composition that contacts the articles to be washed can be referred to as a concentrate or a use composition (or use solution) dependent upon the formulation employed in methods according to the invention.

A use solution may be prepared from the concentrate by diluting the concentrate with water at a dilution ratio that provides a use solution having desired sanitizing and rinsing properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed from treated surfaces and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. Without limiting the scope of invention, the numeric ranges are inclusive of the numbers defining the range and include each integer within the defined range.

The methods of making or formulating the sanitizing rinse aid compositions according to the invention may include combining the nonionic surfactants, carboxylic acids and hydrogen peroxide with the other materials disclosed herein. The compositions can also be formulated with preformed peroxycarboxylic acids. However, preferably the compositions are made by mixing the carboxylic acid or mixture thereof with the hydrogen peroxide to react the mixture and adding the balance of required ingredients to form the sanitizing rinse aid compositions. Exemplary methods are disclosed for example in U.S. Pat. No. 7,887,641, which is herein incorporated by reference in its entirety. Thereafter, a stable equilibrium mixture is produced containing the carboxylic acid(s) with hydrogen peroxide and allowing the mixture to stand for 1-7 days (or greater).

Peroxycarboxylic Acids

According to the invention, a peroxycarboxylic acid (i.e. peracid) is included for antimicrobial efficacy in the sanitizing and rinsing compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid," "peracid" and others used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic acids (e.g., C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, sodium alcoholate or alkyl and aryl esters. Alternatively, peracids can be prepared through non-equilibrium reactions, which may be generated for use in situ, such as the methods disclosed in U.S. Patent Publication Nos. 2012/0172440 and 2012/0172441 each titled "In Situ Generation of Peroxycarboxylic Acids at Alkaline pH, and Methods of Use Thereof," which are incorporated herein by reference in their entirety. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety. In other embodiments, the peroxycarboxylic may be a combination of a short chain peroxycarboxylic acid, including for example peroxyacetic acid and/or a medium chain peroxycarboxylic acid, including for example those disclosed in U.S. Pat. No. 7,887,641, which is herein incorporated by reference in its entirety.

The peroxycarboxylic acid when formed in situ generally follows the reaction of hydrogen peroxide with the carboxylic acid (e.g., octanoic acid or mixture of octanoic acid and acetic acid) as shown below. This reaction is reversible and depending on the pH, water content, and storage temperature, the reaction may take from several hours to several days to reach equilibrium.

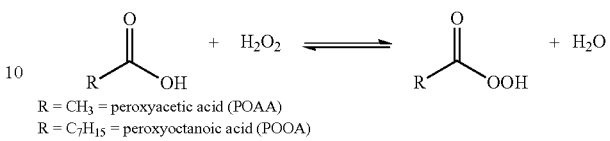

R = $CH_3$ = peroxyacetic acid (POAA)
R = $C_7H_{15}$ = peroxyoctanoic acid (POOA)

In another embodiment, a sulfoperoxycarboxylic acid has the following formula:

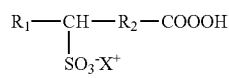

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkylene group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$-$C_{10}$ alkylene group. In some embodiments, $R_2$ is a substituted $C_8$-$C_{10}$ alkylene. In some embodiments, $R_2$ is an unsubstituted $C_6$-$C_9$ alkylene. In other embodiments, $R_2$ is a $C_8$-$C_{10}$ alkylene group substituted with at least one hydroxyl group. In some embodiments, $R_2$ is a $C_{10}$ alkylene group substituted with at least two hydroxyl groups. In other embodiments, $R_2$ is a $C_8$ alkylene group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkylene.

These and other suitable sulfoperoxycarboxylic acid compounds for use in the stabilized peroxycarboxylic acid compositions of the invention are further disclosed in U.S.

Pat. No. 8,344,026 and U.S. Patent Publication Nos. 2010/0048730 and 2012/0052134, which are incorporated herein by reference in its entirety.

In additional embodiments a sulfoperoxycarboxylic acid is combined with a single or mixed peroxycarboxylic acid composition, such as a sulfoperoxycarboxylic acid with peroxyacetic acid and peroxyoctanoic acid (PSOA/POAA/POOA). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above.

Preferably a composition of the invention includes peroxyacetic acid and peroxyoctanoic acid, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are employed, such as disclosed in U.S. Pat. No. 8,344,026 which is incorporated herein by reference in its entirety. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (approximately 15%) available as EnviroSan or Victory (Ecolab, Inc., St. Paul MN). Most commercial peracid solutions state a specific percarboxylic acid concentration without reference to the other chemical components in a use solution. In preferred embodiments, the sanitizing rinse additive compositions exhibit low to no odor in the concentrated formulation. In a further preferred aspect, a low odor peracid is employed, such as peroxyoctanoic acid (POOA), to allow significantly increased concentration of the peracid in the sanitizing rinse aid composition without increasing the odor. According to some preferred embodiments, the peroxycarboxylic acid is not a peroxyacetic acid (containing the corresponding carboxylic acid acetic acid). According to other embodiments, the concentration of POAA in a concentrate composition is less than about 2 wt-%, and preferably less than about 1 wt-%.

In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyacetic acid, peroxyoctanoic acid and/or peroxysulfonated oleic acid.

In an aspect of the invention, a peracid may be selected from a concentrated composition having a ratio of hydrogen peroxide to peracid from about 0:10 to about 10:0, preferably from about 0.5:10 to about 10:0.5, preferably from about 1:8 to 8:1. Various concentrated peracid compositions having the hydrogen peroxide to peracid ratios of about 0.5:10 to about 10:0.5, preferably from about 1:8 to 8:1, may be employed to produce a use solution for treatment according to the methods of the invention. In a further aspect of the invention, a peracid may have a ratio of hydrogen peroxide to peracid as low as from about part hydrogen peroxide to about 1 part peracid. Without limiting the scope of invention, the numeric ranges are inclusive of the numbers defining the range and include each integer within the defined range.

In a preferred aspect, the $C_1$-$C_{22}$ percarboxylic acid can be used at any suitable concentration. In some embodiments, the $C_1$-$C_{22}$ percarboxylic acid has a concentration from about 0.1 wt-% to about 40 wt-% in a concentrated equilibrium composition. In other embodiments, the $C_1$-$C_{22}$ percarboxylic acid has a concentration from about 1 wt-% to about 40 wt-%, or from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, wt-%, 16 wt-%, 17 wt-%, 18 wt-%, 19 wt-%, 20 wt-%, 25 wt-%, 30 wt-%, 35 wt-%, or wt-%. Without limiting the scope of invention, the numeric ranges are inclusive of the numbers defining the range and include each integer within the defined range.

Carboxylic Acids

The present invention includes a carboxylic acid with the peracid composition and hydrogen peroxide. A carboxylic acid includes any compound of the formula R—$(COOH)_n$ in which R can be hydrogen, alkyl, alkenyl, alkyne, acylic, alicyclic group, aryl, heteroaryl, or heterocyclic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems, which are disclosed in U.S. Pat. No. 8,344,026, and U.S. Patent Publication Nos. 2010/0048730 and 2012/0052134, each of which are herein incorporated by reference in their entirety.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has a concentration in an equilibrium composition from about 0.1 wt-% to about 80 wt-%. In other embodiments, the $C_1$-$C_{22}$ carboxylic acid has a concentration from about 1 wt-% to about 80 wt-%. In still other embodiments, the $C_1$-$C_{22}$ carboxylic acid has a concentration at about 1 wt-% to about 40 wt-%, or preferably from about 1 wt-% to about 15 wt-%. Without limiting the scope of invention, the numeric ranges are inclusive of the numbers defining the range and include each integer within the defined range.

Oxidizing Agents

The present invention includes an oxidizing agent for the equilibrium peroxycarboxylic acid, such as hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining an equilibrium between a carboxylic acid, hydrogen peroxide, and a peracid. The amount of hydrogen peroxide should not exceed an amount that would adversely affect the antimicrobial activity of a composition of the invention. In further aspects of the invention, hydrogen peroxide concentration can be significantly reduced within an antimicrobial peracid composition. In some aspects, an advantage of minimizing the concentration of hydrogen peroxide is that antimicrobial activity of a composition of the invention is improved as compared to conventional equilibrium peracid compositions.

Beneficially, in some aspects of the invention, the sanitizing and rinsing compositions using equilibrium peracid compositions are not reliant and/or limited according to any particular ratio of hydrogen peroxide to peracid. In some embodiments the inclusion of a peracid stabilizing agent (e.g. DPA) is suitable for providing peracid stability under varying ratios of hydrogen peroxide to peracid.

The hydrogen peroxide can be used at any suitable concentration. In some embodiments, a concentrated equilibrium composition has a concentration of hydrogen peroxide from about 0.5 wt-% to about 90 wt-%, or from about 1 wt-% to about 90 wt-%. In still other embodiments, the hydrogen peroxide has a concentration from about 1 wt-% to about 80 wt-%, from about 1 wt-% to about 50 wt-%. Without limiting the scope of invention, the numeric ranges are inclusive of the numbers defining the range and include each integer within the defined range.

Surfactants

According to the invention, rinse aid surfactant(s) are included for rinsing efficacy in the sanitizing and rinsing compositions disclosed herein. The rinse aid surfactant(s) are required to provide rinse aid performance, including sheeting, spot- and film-free ware and quick drying performance in the presence of peroxycarboxylic acid and hydrogen peroxide. In further aspects, the rinse aid surfactant(s) provide antifoaming properties to overcome foam generated by agitation of machine sump solutions (e.g. such as those containing proteinaceous food soils). In some embodiments, the rinse aid surfactant(s) are stable and provide such rinse aid performance under acidic conditions and are accordingly referred to as acid-compatible.

In some embodiments, the compositions of the present invention include more than one rinse aid surfactant, and preferably include a combination of at least two rinse aid surfactants. In some embodiments a combination of surfactants is provided wherein one surfactant predominantly provides antifoaming properties, and wherein the second surfactant predominantly aids in sheeting and drying (i.e. wetting surfactant). Surfactants suitable for use with the compositions of the present invention include nonionic surfactants.

In some embodiments, the concentrated compositions of the present invention include about 10 wt-% to about 50 wt-% of a nonionic surfactant. In other embodiments the compositions of the present invention include about 10 wt-% to about 30 wt-% of a nonionic surfactant. In still yet other embodiments, the compositions of the present invention include about 10 wt-% to about 20 wt-% of a nonionic surfactant. In addition, without being limited according to the invention, all ranges are inclusive of the numbers defining the range and include each integer within the defined range.

In some aspects the ratio of the defoaming to wetting surfactants impacts the shelf-life of the sanitizing rinse aid composition according to the invention. In a further aspect, the ratio of the defoaming to wetting surfactants impacts the anti-foaming capabilities of the composition. According to the invention, in preferred aspects, the concentration of the defoaming surfactants exceeds the concentration of the wetting surfactant. In further aspects the ratio is from about 1:1 to about 100:1, preferably from about 1:1 to about 50:1. In some aspects the ratio of the defoaming surfactants to the wetting surfactants is from about 1.5:1 to about 10:1, preferably from about 2:1 to about 5:1. In addition, without being limited according to the invention, all ranges for the ratios recited are inclusive of the numbers defining the range and include each integer within the defined range of ratios.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

In an aspect, preferred nonionic surfactants for use as the defoaming surfactant include block polyoxypropylene-polyoxyethylene polymeric compounds such as alcohol-EO-PO nonionic surfactants. Exemplary alcohol-EO-PO nonionics are commercially available under the tradename Plurafac®. Without being limited to a particular theory of the invention, alcohol-EO-PO surfactants retain antifoaming properties longer than polyoxypropylene-polyoxyethylene polymeric compounds having an EOm-POn-EOm (wherein m is an integer between 1-200, and n is an integer between 1-100) type structure (such as those commercially-available under the tradename Pluronic®, manufactured by BASF Corp.) and compounds having an POm-EOn-POm (wherein m is an integer between 1-100, and n is an integer between 1-200) type structure (such as those commercially-available under the tradename Pluronic® R, also manufactured by BASF Corp.) due to the presence of the peroxycarboxylic acid and hydrogen peroxide in the formulations according to the invention.

A particularly useful group of alcohol alkoxylates are those having the general formula R-(EO)$_m$—(PO)$_n$, wherein m is an integer of about 1-20, preferably 1-10 and n is an integer of about 1-20, preferably 2-20, and wherein R is any suitable radical, including for example a straight chain alkyl group having from about 6-20 carbon atoms.

In a further aspect, preferred nonionic surfactants include capped or end blocked surfactants (wherein the terminal hydroxyl group (or groups)) is capped. In an embodiment, capped aliphatic alcohol alkoxylates include those having end caps including methyl, ethyl, propyl, butyl, benzyl and chlorine and may have a molecular weight of about 400 to about 10,000. Without being limited to a particular theory of the invention, capped nonionic surfactants provide improved stability over PO-EO-PO type or EO-PO-EO type structure nonionics (such as those commercially-available under the tradenames Pluronic® and Pluronic® R, manufactured by BASF Corp). According to the invention, the capping improves the compatibility between the nonionic surfactants and the oxidizing hydrogen peroxide and peroxycarboxylic acids when formulated into a single composition.

In a further aspect, preferred nonionic surfactants for use as the wetting surfactant include alkyl ethoxylates and/or alcohol ethoxylates. In some embodiments, the wetting agent includes one or more alcohol ethoxylate compounds that include an alkyl group that has 12 or fewer carbon atoms. For example, alcohol ethoxylate compounds for use in the sanitizing rinse aids of the present invention may each independently have structure represented by the following formula: R—O—(CH$_2$CH$_2$O)$_n$—H, wherein R is a C$_1$-C$_{16}$ alkyl group and n is an integer in the range of 1 to 100. In other embodiments, R may be a (C$_8$-C$_{12}$) alkyl group, or may be a (C$_8$-C$_{10}$) alkyl group. Similarly, in some embodiments, n is an integer in the range of 1-50, or in the range of 1-30, or in the range of 1-25. In some embodiments, the one or more alcohol ethoxylate compounds are straight chain hydrophobes. An example of such an alcohol ethoxylate wetting surfactant is commercially available from Sasol under the tradename NOVEL® 1012-21 GB.

Alkyl ethoxylate surfactants terminated with methyl, benzyl, and butyl "capping" groups are known, with the methyl and butyl capped versions being commercially available. However, the various alkyl ethoxylates can contain a significant amount of unprotected (i.e., uncapped) hydroxyl groups. Therefore, there is a preference for use of the alkyl ethoxylate surfactants to be capped to remove the reactivity of unprotected hydroxyl groups. In a further embodiment, the surfactant has only a single uncapped hydroxyl group, such as the following exemplary structures: Alkyl-(EO)m-(PO)n-POH and Alkyl-(EO)n-EOR, wherein R=alkyl (60-80%), R=H (20-40%), and wherein m is an integer in the range from 1 to 20 and n is an integer in the range from 1 to 20.

In some embodiments, the defoaming and wetting surfactants used can be chosen such that they have certain characteristics, for example, are environmentally friendly, are suitable for use in food service industries, and/or the like. For example, the particular alcohol ethoxylates used in the sheeting agent may meet environmental or food service regulatory requirements, for example, biodegradability requirements. In a preferred aspect, the nonionic surfactants employed in the sanitizing rinse aid compositions are approved by the U.S. EPA under CFR 180.940 for use in food contact sanitizers. Additional nonionic surfactants include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

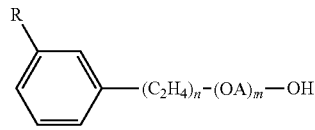

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R_2CON_{R_1}Z$ in which: $R_1$ is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-Cis mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

13. A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$—$(PO)_SN$-$(EO)_tH$, $R^{20}$—$(PO)_SN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20 preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)$v-$N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

14. Amine oxides are tertiary amine oxides corresponding to the general formula:

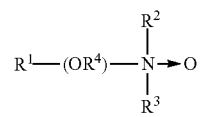

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

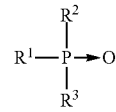

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

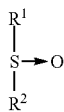

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Additional Functional Ingredients

The components of the sanitizing and rinsing compositions can further be combined with various functional components suitable for use in ware wash and other sanitizing applications. In some embodiments, the compositions including the peroxycarboxylic acid, carboxylic acid, hydrogen peroxide, solvent and/or water, and/or rinse aid surfactants make up a large amount, or even substantially all of the total weight of the sanitizing and rinsing composition. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in cleaning, specifically ware wash applications. However, other embodiments may include functional ingredients for use in other applications.

In other embodiments, the compositions may include defoaming agents, anionic surfactants, fluorescent tracers (including those disclosed for example in U.S. patent application Ser. No. 13/785,405, which is incorporated herein by reference), anti-redeposition agents, bleaching agents, solubility modifiers, dispersants, additional rinse aids, antiredeposition agents, metal protecting agents and/or etch protection convention for use in warewashing applications, stabilizing agents, corrosion inhibitors, additional sequestrants and/or chelating agents, humectants, pH modifiers, fragrances and/or dyes, rheology modifiers or thickeners, hydrotropes or couplers, buffers, solvents and the like, such as those disclosed in U.S. Publication No. 2012/0225805, which is herein incorporated by reference in its entirety.

Hydrotropes or Couplers

In some embodiments, the compositions of the present invention can include a hydrotrope or coupler. These may be used to aid in maintaining the solubility of the wetting and/or defoaming surfactants as well as a coupling agent for the peroxycarboxylic acid components. In some embodiments, hydrotropes are low molecular weight n-octane sulfonate and aromatic sulfonate materials such as alkyl benzene sulfonate, xylene sulfonates, naphthalene sulfonate, dialkyldiphenyl oxide sulfonate materials, and cumene sulfonates.

A hydrotrope or combination of hydrotropes can be present in the compositions at an amount of from between about 1 wt-% to about 50 wt-%. In other embodiments, a hydrotrope or combination of hydrotropes can be present at about 10 wt-% to about 40 wt-% of the composition. Without limiting the scope of invention, the numeric ranges are inclusive of the numbers defining the range and include each integer within the defined range.

Peracid Stabilizing Agent

A peracid stabilizing agent or agents may be included in compositions according to the invention. Beneficially, the peracid stabilizing agent(s) prevents the decomposition of peracid in an equilibrium peracid composition. In addition, peracid stabilizing agent(s) may prevent an equilibrium peracid composition from exceeding reaching their self-accelerating decomposition temperatures (SADT).

Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In some embodiments, the compositions of the present invention include dipicolinic acid as a stabilizing agent. Compositions including dipicolinic acid can be formulated to be free or substantially free of phosphorous. In an aspect of the invention, the stabilizing agent is a pyridine carboxylic acid compound. Pyridine carboxylic acids include dipicolinic acids, including for example, 2,6-pyridinedicarboxylic acid (DPA). In a further aspect, the stabilizing agent is a picolinic acid, or a salt thereof. In an aspect of the invention, the stabilizing agent is a picolinic acid or a compound having the following Formula (IA):

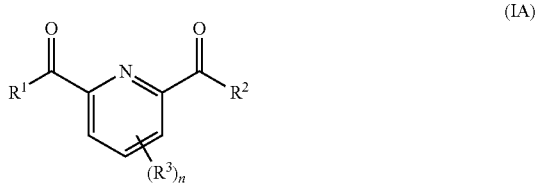

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a further aspect of the invention, the peracid stabilizing agent is a compound having the following Formula (IB):

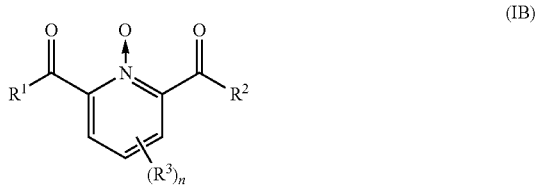

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof. Dipicolinic acid has been used as a stabilizer for peracid compositions, such as disclosed in WO 91/07375 and U.S. Pat. No. 2,609,391, which are herein incorporated by reference in their entirety.

In a further aspect, the stabilizing agent is a phosphate stabilizer or a phosphonate based stabilizer, such as Dequest 2010. Phosphate based stabilizers are known to act as metal chelators or sequestrants. Conventional phosphate based stabilizing agents include for example, 1-hydroxy ethylidene-1,1-diphosphonic acid ($CH_3C(PO_3H_2)_2OH$) (HEDP). In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present invention.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)]available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit® AM.

According to various embodiments of the invention, the stabilizing agent can be or include aminocarboxylic acid type sequestrants. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

According to still further embodiments of the invention, the stabilizing agent can be or include The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In other embodiments the stabilizing agent may be a low-phosphate or a phosphate-free stabilizer to provide either low-phosphate or phosphate-free sanitizing and rinsing compositions.

In a still further aspect, a combination of more than one stabilizing agent may be employed. Stabilizing agent(s) may be present in amounts sufficient to provide the intended stabilizing benefits, namely achieving the desired shelf life and/or elevating the SADT of a concentrated peroxycarboxylic acid composition. Peracid stabilizing agents may be present in a concentrated equilibrium peracid composition in amounts from about wt-% to about 25 wt-%, 0.01 wt-% to about 10 wt-%, and more preferably from about 0.1 wt-% to about 10 wt-%. Without limiting the scope of invention, the numeric ranges are inclusive of the numbers defining the range and include each integer within the defined range.

Defoaming Agent

The present invention may include a defoaming agent. Defoaming agents suitable for use in the peroxycarboxylic acid compositions according to the invention are compatible with peracid compositions and the nonionic surfactants in the single, dual functioning sanitizing and rinsing formulations. The defoaming agents suitable for use in the peroxycarboxylic acid compositions according to the invention, maintain a low foam profile under various water conditions, preferably under deionized or soft water conditions, and/or under mechanical action. In a still further aspect, the defoaming agents are compatible with surfactants, preferably anionic surfactants, to achieve critical performance such as coupling/wetting, improved material compatibility and enhanced biocidal efficacy. In preferred aspects, the defoaming agent provides a synergistic biocidal efficacy.

In an aspect of the invention, the defoaming agent is a metal salt, including for example, aluminum, magnesium, calcium, zinc and/or other rare earth metal salts. In a preferred aspect, the defoaming agent is a cation with high charge density, such as $Fe^{3+}$, $Al^{3+}$ and $La^{3+}$. In a preferred aspect, the defoaming agent is aluminum sulfate. In other aspects, the defoaming agent is not a transition metal compound. In some embodiments, the compositions of the present invention can include antifoaming agents or defoamers which are of food grade quality, including for example silicone-based products, given the application of the method of the invention.

In an aspect of the invention, the defoaming agent can be used at any suitable concentration to provide defoaming with the surfactants according to the invention. In some embodiments, a concentrated equilibrium composition has a concentration of the a defoaming agent from about 0.001 wt-% to about 10 wt-%, or from about 0.1 wt-% to about 5 wt-%. In still other embodiments, the defoaming agent has a concentration from about 0.1 wt-% to about 1 wt-%. Without limiting the scope of invention, the numeric ranges are inclusive of the numbers defining the range and include each integer within the defined range.

Anti-Redeposition Agents

The sanitizing rinse aid compositions can optionally include an anti-redeposition agent capable of facilitating sustained suspension of soils in a rinse solution and preventing removed soils from being redeposited onto the substrate being rinsed. Some examples of suitable anti-redeposition agents can include fatty acid amides, fluorocarbon surfactants, complex phosphate esters, styrene maleic anhydride copolymers, and cellulosic derivatives such as hydroxyethyl cellulose, hydroxypropyl cellulose, and the like. A rinse aid composition may include up to about 10 wt-% of an anti-redeposition agent.

Methods of Use

In an aspect, the present invention includes use of the compositions for sanitizing and rinsing surfaces and/or products. In another aspect, the compositions of the invention are particularly suitable for use as a hard surface cleaner and/or sanitizer, food contact sanitizer (including direct or indirect contact sanitizer), tissue contact sanitizer (including for example fruits and vegetables), fast drying sanitizer for various hard surfaces (including for example healthcare surfaces, instruments, food and/or beverage surfaces, processing surfaces, and the like), any-streaking or smearing hard surface sanitizer, and the like. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The methods of use are particularly suitable for warewashing. Suitable methods for using the sanitizing rinse aid compositions for warewashing are set forth in U.S. Pat. No. 5,578,134, which is herein incorporated by reference in its entirety. Beneficially, according to various embodiments of the invention, the methods provide the following unexpected benefits: decrease in utilities for a warewashing machine to the those expected of commercially-available low temperature ware wash machines, including door machines; utility consumption equivalent to dish machines employed for chlorine-based sanitizing, including for example commercially-available 120 Volt, 30 Amp dishwash machines; and suitable for use with a single, dual-functioning composition containing a detergent(s), rinse additive(s) and an optional additional functional component for sanitizing and/or rinsing. In still further embodiments of the invention, the methods for warewashing may additionally provide any one or more of the following unexpected benefits for warewashing applications: improved ware washing results (including sanitizing efficacy and/or rinsing); decreased total utility costs for door dishmachines; elimination of any need for rewashing of wares; chlorine-free formulations; and/or low phosphorous formulations or substantially phosphorous-free formulations.

Exemplary articles in the warewashing industry that can be treated with a sanitizing rinse aid composition according to the invention include plastics, dishware, cups, glasses, flatware, and cookware. For the purposes of this invention, the terms "dish" and "ware" are used in the broadest sense to refer to various types of articles used in the preparation, serving, consumption, and disposal of food stuffs including pots, pans, trays, pitchers, bowls, plates, saucers, cups, glasses, forks, knives, spoons, spatulas, and other glass, metal, ceramic, plastic composite articles commonly available in the institutional or household kitchen or dining room. In general, these types of articles can be referred to as food or beverage contacting articles because they have surfaces which are provided for contacting food and/or beverage. When used in these warewashing applications, the rinse aid should provide effective sheeting action and low foaming properties. In addition to having the desirable properties described above, it may also be useful for the sanitizing rinse aid composition to be biodegradable, environmentally friendly, and generally nontoxic. A rinse aid of this type may be described as being "food grade".

The methods of use are suitable for treating a variety of surfaces, products and/or target in addition to ware. For example, these may include a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

In a still further embodiment, the methods of the invention are suitable for meeting various regulatory standards, including for example EPA food contact sanitizers requiring at least a 5 log reduction in pathogenic microorganisms in 30 seconds and/or NSF standards similarly requiring at least a 5 log reduction in treated pathogenic microorganisms. In still further aspects, without limiting the scope of the invention, the methods of the invention may provide sufficient sanitizing efficacy at conditions more or less strenuous than such regulatory standards.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment.

The various methods of treatment can include the use of any suitable level of the peroxycarboxylic acid. In some embodiments, the treated target composition comprises from about 1 ppm to about 1000 ppm of the peroxycarboxylic acid when diluted for use, including any of the peroxycarboxylic acid compositions according to the invention. The various applications of use described herein provide the peroxycarboxylic acid compositions to a surface and/or product in need of sanitizing and rinsing. Beneficially, the compositions of the invention are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be about 15 seconds, at least about 15 seconds, about 30 seconds or greater than 30 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of peracid in a use solution.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about including at about 37° C., from about 41° C. to about 50° C., from about 51° C. to about or from about 61° C. to about 82° C., or at increased temperatures there above suitable for a particular application of use.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms, gram positive and gram negative microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one $\log_{10}$. In other embodiments, the present methods can be used to reduce the microbial population in and/or on the target or the treated target composition by at least two $\log_{10}$. In still other embodiments, the present methods can be used to reduce the microbial population in and/or on the target or the treated target composition by at least three $\log_{10}$. In still other embodiments, the present methods can be used to reduce the microbial population in and/or on the target or the treated target composition by at least five $\log_{10}$. Without limiting the scope of invention, the numeric ranges are inclusive of the numbers defining the range and include each integer within the defined range.

The peroxycarboxylic acid compositions may include concentrate compositions or may be diluted to form use compositions. In general, a concentrate refers to a composition that is intended to be diluted with water to provide a use solution that contacts a surface and/or product in need of treatment to provide the desired cleaning, sanitizing or the like. The peroxycarboxylic acid composition that contacts the surface and/or product in need of treatment can be referred to as a concentrate or a use composition (or use solution) dependent upon the formulation employed in methods according to the invention. It should be understood that the concentration of the peroxycarboxylic acid in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In a preferred aspect, the highly concentrated peroxycarboxylic acid of the sanitizing rinse additive composition is diluted from about 0.001% (wt/vol.) to about 2% (wt/vol.), or from about 0.001% (wt/vol.) to about 1% (wt/vol.), or from about 0.01% (wt/vol.) to about 0.05% (wt/vol.), and preferably to approximately 0.025% (wt/vol.). Without being limited to a particular dilution of the concentrated sanitizing rinse additive composition, in some aspects this dilution corresponds to approximately 0.5 mL to about 3 mL of the liquid concentrate per dish machine cycle (as one skilled in the art understands to further dependent on the rinse water volume of the dish machine). Without limiting the scope of invention, the numeric ranges are inclusive of the numbers defining the range and include each integer within the defined range.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The biocidal efficacy of various equilibrium peroxycarboxylic acid compositions shown in Table 2 according to the invention were evaluated to demonstrate the effect of temperature on the peroxycarboxylic acid efficacy. AOAC Official Method 960.09 (Germicidal and Detergent Sanitizing Action of Disinfectants) was employed to test the compositions. The testing was conducted on a POOA based sanitizer (commercially-available under the tradename Octave™, Ecolab Inc.) having approximately 1 wt-% POOA and 7.5 wt-% hydrogen peroxide. The POOA sanitizer was tested at different concentrations (5, 8, and 12 ppm active POOA), different pH levels (3.5 and 5.5) and different temperatures relevant applicable to commercial ware washing (120° F. and 140° F.). The results are set forth in Table 2.

TABLE 2

| Concentration (ppm POOA) | Use-solution pH | Use-solution Temperature | Avg. $Log_{10}$ Reduction in 30 sec |  |
|---|---|---|---|---|
|  |  |  | S. aureus | E. coli |
| 5 ppm | pH 3.50 | 120° F. | 7.10 | >7.01 |
|  | pH 5.50 |  | 5.84 | 1.67 |
| 8 ppm | pH 3.50 |  | 6.40 | >7.01 |
|  | pH 5.50 |  | >7.10 | 1.99 |
| 12 ppm | pH 3.50 |  | >7.10 | >7.01 |
|  | pH 5.50 |  | 6.68 | >7.01 |
| 5 ppm | pH 3.50 | 140° F. | >7.12 | >6.97 |
|  | pH 5.50 |  | >7.12 | 4.58 |
| 8 ppm | pH 3.50 |  | >7.12 | >6.97 |
|  | pH 5.50 |  | >7.12 | >6.97 |
| 12 ppm | pH 3.50 |  | >7.12 | >6.97 |
|  | pH 5.50 |  | >7.12 | >6.97 |

As shown in Table 2, at pH 3.5, complete *E. coli* kill was achieved regardless of POOA concentration or temperature. However at pH 5.5, only the highest concentration of POOA (12 ppm) was able to achieve complete kill 120° F. Repeating the experiment at 140° F. resulted in complete kill at 8 ppm POOA and an improvement of approximately 3 log for the 5 ppm POOA dilution.

Example 2

Various sanitizing rinse aid formulations were prepared by mixing the components described in Table 3.

TABLE 3

| Component | Formulation ID 13505-29-01 Wt-% |
|---|---|
| $H_2O_2$ (50%) | 1-80 |
| Octanoic acid | 1-10 |
| Acetic acid | 1-10 |
| Dequest 2010 | 1-10 |
| SXS (40%) | 10-25 |
| Pluronic 25R2 | 1-25 |
| Novel 1021 GB | 1-20 |
| Total | 100.00 |

The rinse aid surfactants Pluronic 25R2 and Novel 1021 GB were used as the antifoaming and rinse aid imparting surfactants in initial formulations of the concentrated compositions. The composition set forth in Table 3 exhibited sufficient initial stability and antifoaming properties. However, the surfactants demonstrated reaction with the generated peracid and/or hydrogen peroxide of the formulations. This reaction was accelerated at elevated temperatures, e.g., 40° C., and ultimately resulted in phase separation of the concentrates and/or degradation of the antifoaming properties imparted by antifoaming surfactant Pluronic 25R2 in comparison to the initial concentrated composition. Without being limited to a particular theory of the invention, a potential mechanism of action of such reaction with the peracid and/or hydrogen peroxide is the terminal alcohol functional groups of the surfactants acting as reaction points (e.g., alcohols demonstrated limited stability in the presence of hydrogen peroxide and peroxycarboxylic acids).

Due to the reaction of the surfactants with the peracid and/or hydrogen peroxide, the Pluronic type surfactant having two terminal hydroxyl functional groups per molecule was replaced with a surfactant having only one terminal hydroxyl group to determine whether improved stability resulted.

The Glewwe foam test method was used to identify other surfactants with similar antifoaming properties to Pluronic 25R2 that could be screened for potentially improved stability to peracid chemistries in the sanitizing rinse aid compositions according to the invention.

A Glewwe Foam meter provides a dynamic foam test rather than a static test (as in the case of the Ross-Miles foam test). A dynamic foam meter is considered more appropriate for simulation of industrial conditions, e.g., the conditions in a dish machine. The equipment and general procedure for the Glewwe form test is described in U.S. Pat. No. 3,899,387, column 12, line 45 et seq, which is herein incorporated by reference in its entirety. The foam meter itself consists of a thermostated reservoir and a pump to recirculate the aqueous medium with foaming tendencies. The foam developed by the action of the aqueous stream impinging on the surface in the reservoir causes foam formation.

The foam heights of the tested compositions were determined using the following method. First 3000 mL of each formula was prepared and gently poured into Glewwe cylinder. The foam height is measured after various time intervals and provides a relative measure of the effectiveness of the defoamer. The reservoir of this foam meter consists of a stainless steel laboratory beaker of 3,000 mL capacity.

Sealed to this beaker by means of a silicone sealant is a clear Plexiglass tubing which snugly fits into the inner walls of the beaker. This enables the operator to measure the foam height above the liquor level. The beaker measures about 19 cm high by about 17 to 18 cm in diameter and the Plexiglass tube extends about 30 to 35 cm above the lip of this beaker. Further detail regarding the Glewwe foam test is shown in, U.S. Pat. No. 5,447,648, which is expressly incorporated by reference herein.

A ruler was attached to the side of the cylinder, and the solution was level with the bottom of the ruler. The pump was turned on. Foam height was estimated by reading the average level of foaming according to the ruler. Foam height readings were taken versus time with a stopwatch or timer. The pump was turned off and height of the foam was recorded at various times.

The results are shown in Table 4. All surfactants were tested at 50 ppm and the temperature was 120° F. Surfactants shown in italicized font in Table 4 exhibited substantially similar antifoaming properties as Pluronic 25R2. Formulations were prepared using these lead candidates and monitored for phase stability properties over time while stored at elevated temperature (either 40° C. or 50° C.).

TABLE 4

| Surfactant | Foam height after 1 min run time (inches) | | | Foam height after 5 (total) minutes run time | | | 180.940 Approved |
|---|---|---|---|---|---|---|---|
| | initial | 15 sec | 1 min | initial | 15 sec | 1 min | |
| *Pluronic 25R2* | *trace* | *0.00* | *0.00* | *0.50* | *0.00* | *0.00* | *Y* |
| Genapol EP 2454 | trace | trace | trace | 3.00 | 1.50 | 1.00 | Y |
| Genapol EP 2544 | trace | 0.00 | 0.00 | 2.75 | 0.75 | 0.50 | unknown |
| Plurafac RA-40 | trace | 0.00 | 0.00 | 2.00 | 0.25 | trace | Y |
| DEHYPON LS-36; Surfonic LF-42 | trace | 0.00 | 0.00 | 3.00 | 0.50 | trace | Y |
| Plurafac LF-500 | trace | 0.00 | 0.00 | 1.75 | trace | trace | Y |
| Genapol EP 2584 (EU) | 3.00 | 1.00 | 0.25 | 8.00 | 6.00 | 3.00 | Y |
| *Plurafac S305 LF* | *trace* | *0.00* | *0.00* | *0.50* | *0.00* | *0.00* | *Y* |
| *Plurafac SLF 18/ Surfonic LF-18* | *trace* | *0.00* | *0.00* | *0.50* | *0.00* | *0.00* | *Y* |
| *Plurafac SLF 180* | *trace* | *0.00* | *0.00* | *0.50* | *0.00* | *0.00* | *Y* |
| Pluronic L61 | trace | 0.00 | 0.00 | 2.00 | trace | 0.00 | Y |
| *Pluronic L81* | *trace* | *0.00* | *0.00* | *1.00* | *0.00* | *0.00* | *Y* |
| Pluronic L101 | trace | 0.00 | 0.00 | 4.00 | 3.50 | 2.00 | Y |
| Tergitol L 61 | trace | 0.00 | 0.00 | 2.00 | 0.50 | 0.00 | Y |
| Tergitol L 62 | 2.00 | 1.00 | 0.50 | 8.00 | 6.00 | 3.00 | Y |
| 13505-58-2 | 2.00 | 1.00 | 0.50 | 11.00 | 10.00 | 7.00 | N/A |
| D0-97 | 1.00 | 0.50 | 0.50 | 1.00 | 0.00 | 0.00 | Y |
| LD-097 | 1.50 | 0.00 | 0.00 | 3.50 | 1.00 | 0.00 | Y |
| LF-45 | 0.50 | trace | trace | 3.00 | 1.00 | 1.00 | Y |
| LD-97 | 1.00 | 0.00 | 0.00 | 2.00 | 0.00 | 0.00 | Y |
| *D-500* | *1.00* | *trace* | *trace* | *1.00* | *0.00* | *0.00* | *Y* |
| Plurafac LF 431 (capped) | 1.00 | 0.50 | trace | 2.00 | 0.50 | 0.50 | N |
| Plurafac LF 132 (capped) | trace | 0.00 | 0.00 | 4.00 | 1.00 | 0.50 | N |
| Plurafac LF 131 (capped) | trace | 0.00 | 0.00 | 2.25 | trace | 0.00 | N |
| Plurafac LF 231 (capped) | 0.50 | trace | trace | 2.00 | trace | trace | N |

Exemplary tested formulations employing commercially available nonionic surfactants are shown in Table 5.

TABLE 5

| | Formula ID | | | | | | | | |
|---|---|---|---|---|---|---|---|---|---|
| | 13505-29-01 | 13505-77-04 | 13505-77-05 | 13505-77-06 | 13505-77-07 | 13505-77-08 | 13508-77-09 | 13505-77-10 | 13505-77-11 |
| H2O2 (50%) | 40-60 | 30-50 | 30-50 | 30-50 | 30-50 | 30-50 | 30-50 | 30-50 | 30-50 |
| Octanoic acid | 1-10 | 1-10 | 1-10 | 1-10 | 1-10 | 1-10 | 1-10 | 1-10 | 1-10 |
| Acetic acid | 1-5 | 1-5 | 1-5 | 1-5 | 1-5 | 1-5 | 1-5 | 1-5 | 1-5 |
| DPA | 0.00 | 0.01-0.2 | 0.01-0.2 | 0.01-0.2 | 0.01-0.2 | 0.01-0.2 | 0.01-0.2 | 0.01-0.2 | 0.01-0.2 |
| Dequest 2010 | 2-5 | 1-5 | 1-5 | 1-5 | 1-5 | 1-5 | 2-5 | 2-5 | 2-5 |
| SXS (40%) | 20-30 | 35-45 | 30-40 | 35-45 | 30-40 | 30-40 | 30-40 | 30-40 | 30-40 |
| Water | 0.00 | 0.00 | 0.00 | 0.00 | 0.00 | 0.00 | 0.00 | 0.00 | 0.00 |
| Plurafac SLF-18 | 0.00 | 5-10 | 10-20 | 0.00 | 0.00 | 0.00 | 0.00 | 0.00 | 0.00 |
| Plurafac S305 LF | 0.00 | 0.00 | 0.00 | 5-10 | 10-20 | 0.00 | 0.00 | 0.00 | 0.00 |
| Plurafac SLF-180 | 0.00 | 0.00 | 0.00 | 0.00 | 0.00 | 5-10 | 10-20 | 0.00 | 0.00 |

TABLE 5-continued

| | | | | | | | | | |
|---|---|---|---|---|---|---|---|---|---|
| Pluronic 25R2 | 5-15 | 0.00 | 0.00 | 0.00 | 0.00 | 0.00 | 0.00 | 5-10 | 10-20 |
| D-500 | 0.00 | 0.00 | 0.00 | 0.00 | 0.00 | 0.00 | 0.00 | 0.00 | 0.00 |
| Novel 1021 GB | 1-10 | 0.00 | 0.00 | 0.00 | 0.00 | 0.00 | 0.00 | 0.00 | 0.00 |
| Total | 100.00 | 100.00 | 100.00 | 100.00 | 100.00 | 100.00 | 100.00 | 100.00 | 100.00 |
| Phase Stable 4 wks @ 40° C. | N | Y | Y | Y | Y | Y | Y | N | N |

| | Formula ID | | | | | | |
|---|---|---|---|---|---|---|---|
| | 13505-78-02 | 13505-78-04 | 13505-78-06 | 13505-80-02 | 13505-82-12 | 13505-84-05 | 13642-08-01 |
| H2O2 (50%) | 30-50 | 30-50 | 30-50 | 30-50 | 30-50 | 30-50 | 30-50 |
| Octanoic acid | 1-10 | 1-10 | 1-10 | 1-10 | 1-10 | 1-10 | 1-10 |
| Acetic acid | 2-6 | 2-6 | 2.25 | 0.00 | 1-5 | 1-5 | 0.00 |
| DPA | 0.01-0.2 | 0.01-0.2 | 0.01-0.2 | 0.01-0.2 | 0.01-0.2 | 0.01-0.2 | 0.01-0.2 |
| Dequest 2010 | 2-5 | 2-5 | 2-5 | 2-5 | 2-5 | 2-5 | 2-5 |
| SXS (40%) | 30-40 | 30-40 | 30-40 | 30-40 | 30-40 | 30-40 | 30-40 |
| Water | 0.00 | 0.00 | 0.00 | 1-5 | 0.00 | 0.00 | 0.00 |
| Plurafac SLF-18 | 5-15 | 0.00 | 0.00 | 5-15 | 0.00 | 0.00 | 0.00 |
| Plurafac S305 LF | 0.00 | 5-15 | 0.00 | 0.00 | 0.00 | 0.00 | 0.00 |
| Plurafac SLF-180 | 0.00 | 0.00 | 5-15 | 0.00 | 0.00 | 5-15 | 5-15 |
| Pluronic 25R2 | 0.00 | 0.00 | 0.00 | 0.00 | 0.00 | 0.00 | 0.00 |
| D-500 | 0.00 | 0.00 | 0.00 | 0.00 | 5-15 | 0.00 | 0.00 |
| Novel 1021 GB | 1-10 | 1-10 | 1-10 | 0.00 | 1-10 | 1-10 | 1-10 |
| Total | 100.00 | 100.00 | 100.00 | 100.00 | 100.00 | 100.00 | 100.00 |
| Phase Stable 4 wks @ 40° C. | Y | Y | Y | Y | Y | Y | Y |

The results shown in Table 5 demonstrate that the "antifoaming" surfactants evaluated, showed improved results when employing a nonionic surfactant with an alkyl-EO-PO type structure having a single hydroxyl functional group per molecule (such as those commercially-available as the Plurafac®-types of surfactants), which demonstrated increased phase stability over the non-alkyl-EO-PO type structures or reverse Pluronic surfactants tested.

The improved stability of the alkyl-EO-PO surfactants supports the proposed, non-limiting, mechanism of action of the hydroxyl groups on the surfactants being the reactive sites leading to instability with the peroxycarboxylic acids and/or hydrogen peroxide of the sanitizing rinse aid formulations. Accordingly, the protection of the hydroxyl end group(s) by capping with an alkyl group leads to unexpected improvements in stabilizing the nonionic surfactants of the peroxycarboxylic acid sanitizing rinse aid compositions. This increase in stability by protecting the hydroxyl end group(s) by capping with an alkyl group was further analyzed using the following structures to determine impact on phase stability as shown in Table 6.

Example 3

Based on the stability data obtained from Example 2 largely dependent on the formulation of the defoaming nonionic surfactant of the sanitizing rinse aid composition, additional testing on the formulation of the wetting surfactant was completed. The wetting surfactant is further needed as a coupling agent for the peroxycarboxylic acid component of the sanitizing rinse aid composition.

The ability of various wetting nonionic surfactants was analyzed to confirm ability to retain coupling power when formulated into the one part sanitizing rinse aid formulations according to the invention. As shown in Table 7, the phase stability and antifoam property results for formulations utilizing various nonionic surfactants were evaluated. NAS-FAL refers to sodium octanesulfonate (NAS-FAL) and Novel 1021 refers to a commercially-available alcohol ethoxylate (Sasol), which were combined as coupling agents with both capped (e.g., Plurafac LF 131) and non-capped (e.g., Plurafac SLF-180) antifoaming surfactants.

TABLE 6

| Example Formula ID | Surfactant (15% in formula) | Surfactant structure | Days phase stable @ 50° C. |
|---|---|---|---|
| 13505-29-01 | Pluronic 25R2 | HOP—(PO)$n$—(EO)$m$—(PO)$n$—POH | 5-7 |
| 13642-16-01 | Plurafac SLF-180 | Alkyl—(EO)$n$—(PO)$n$—POH | 9-12 |
| 13642-16-05 | Plurafac LF 131 | Alkyl—(EO)$n$—EOR* | 16-18 |

*R = alkyl (60-80%),
R = H (20-40%)

TABLE 7

| ID | Surfactant composition in Formula | Days phase stable 122 F. | Days phase stable 100 F. | Anti-Foam Stability (7 d @ 50 C.) Pass/Fail | Anti-Foam Stability (30 d @ 40 C.) Pass/Fail |
|---|---|---|---|---|---|
| 13642-16-01 | 15% SLF-180 | 9-11 | 36-39 | Pass | * |
| 13642-16-02 | 12% SLF-180 + 3% Novel1012 | 9-11 | 46 | Pass | * |
| 13642-16-03 | 12% SLF-180 + 3% Novel810 | 9-11 | 46 | Pass | * |
| 13642-16-04 | 12% SLF-180 + 3% Novel TDA | 9-11 | 46 | Fail | * |
| 13642-16-09 | 14% SLF-180 + 1% NAS-FAL | 12 | 107+ | Pass | Pass |
| 13642-16-10 | 13% SLF-180 + 2% NAS-FAL | 15 | 197 (ongoing) | Pass | Pass |
| 13642-06-09 | 12% SLF-180 + 3% NAS-FAL | 18-20 | 216 (ongoing) | Fail | * |
| 13642-16-05 | 15% LF 131 | 16-18 | 107-109 | Pass | * |
| 13642-16-06 | 12% LF 131 + 3% Novel1012 | 19 | 104 | Fail | * |
| 13642-16-07 | 12% LF 131 + 3% Novel810 | 19 | 107+ | Fail | Fail |
| 13642-16-08 | 12% LF 131 + 3% Novel TDA | 19 | 68 | Fail | Fail |
| 13642-16-11 | 14% LF 131 + 1% NAS-FAL | 23-25 | 197 (ongoing) | Fail | Fail |
| 13642-16-12 | 13% LF 131 + 2% NAS-FAL | 30-32 | 197 (ongoing) | Fail | Fail |

* not tested;
Note:
NAS-FAL level indicated are active level

As shown in Table 7, both wetting surfactants significantly improved phase stability over systems without the second wetting surfactant component, with NAS-FAL providing the best phase stability (e.g., 23-25 days at 50° C.) with the least impact on foam generation. The alkyl capped EO-PO surfactants outperform PO-EO-PO and EO-PO-EO even without the second surfactant in the sanitizing rinse aid compositions. The alkyl capped EO-PO surfactants also outperform the PO-EO-PO (Pluronic 25R2) in combination with the second surfactant (Novel). Systems with alkyl capped antifoaming agents (Plurafac LF131) and NAS-FAL achieved the greatest phase stability at 50° C., but exhibited greater amount of foam than systems using Plurafac SLF-180 as the antifoaming surfactant. The results demonstrate that an alkyl capped surfactant provides suitable peracid stability and antifoaming properties, including shelf stability for at least one year at room temperature. The results are further shown in FIG. 1, wherein the foam performance at 122° F. after storage at 104° F. was evaluated using the various surfactants (FIG. 1). As shown in the figure the foam performance was measured at 13 days, 17 days, 25 days and 28 days.

Example 4

Sanitizing rinse aid compositions according to the invention and resulting from the testing set forth in Example 2 were further evaluated for water sheeting ability, spot free drying on wares, and antimicrobial efficacy in solutions and also on surfaces. The control for the rinse aid component of the sanitizing rinse aid compositions was Apex RA (commercially-available rinse aid additive from Ecolab, Inc.). The control rinse aid formulation includes a combination of the following nonionic rinse aid surfactants, in addition to various functional ingredients not contributing to rinse aid performance: a block co-polymer comprised of polypropoxylate (PO) and polyethoxylate (EO) units having the following general structure POH—$(PO)_n$-$(EO)_m$—$(PO)_n$—POH (Pluronic 25R2, manufactured by BASF, wherein n is an integer from 1-30, m is an integer from 1-160); and an alcohol ethoxylate.

Sheeting performance was evaluated according to the ability of a rinse aid to impart water sheeting on surfaces relevant to commercial ware washing process. The test involves observation of water sheeting on six different types of ware wash materials, including: a china dinner plate, a melamine dinner plate, a glass panel, a stainless steel panel, a stainless steel butter knife, and a 10 oz. glass tumbler. The test materials are initially cleaned and then soiled with a solution containing 0.2% hotpoint soil (mixture of powdered milk and margarine). The materials are then exposed to 30 second wash cycles using 160° F. city water (for high temperature evaluations) or 120° and 140° F. city water (for low temperature evaluations). The test product is measured in ppm actives. Immediately after the ware wash materials are exposed to the test product, the appearance of the water draining off of the individual test materials (sheeting) is examined.

The machine employed is a warewashing machine with hot city water connections and a tempered glass window for observing sheeting on the test substrates. A trouble light is used to light the interior of the warewashing machine so that the test substrates can be easily observed for water sheeting. The warewashing machine has controls for adjusting and maintaining a constant temperature throughout the test. The six test substrates are evenly distributed on a wash rack.

The results of these tests are shown in Table 8.

TABLE 8A

| (13505-84-1 (15% Plurafac SLF-180, 0% Novel 1021 GB)) | | | | | | | | |
|---|---|---|---|---|---|---|---|---|
| ppm, Actives in Rinse Aid | 60 | 70 | 80 | 90 | 100 | 110 | 120 | 130 |
| Polycarbonate Tile (clear) New | | 1 | 1 | 1 | 1 | 1 | 1 | 1 |
| Glass tumbler | | 1 | 1 | 1 | 1 | 1 | X | X |
| China Plate | | 1 | 1 | 1 | 1 | 1 | X | X |
| Melamine Plate | | 1 | 1 | 1 | 1 | 1 | X | X |
| Polypropylene Cup (yellow) | | 1 | 1 | 1 | 1 | 1 | 1 | 1 |
| Dinex Bowl (blue) | | 1 | 1 | 1 | 1 | 1 | 1 | 1 |
| Polypropylene Jug (blue) | | 1 | 1 | 1 | 1 | 1 | 1 | 1 |
| Stainless Steel Knife | | 1 | 1 | 1 | 1 | 1 | 1 | 1 |
| Polypropylene tray (peach) New | | 1 | 1 | 1 | 1 | 1 | 1 | 1 |
| Fiberglass tray (tan) New | | 1 | 1 | 1 | 1 | 1 | 1 | 1 |
| Stainless steel slide 316 New | | 1 | 1 | 1 | 1 | X | X | X |
| Temperature, ° F. | | 140° F. | 140° F. | 140° F. | 140° F. | 140° F. | 140° F. | 140° F. |
| Suds | | Trace | Trace | Trace | 1/4" | 1/4" | 1/4" | 1/4" |

TABLE 8B

| (13505-84-5 (11% Plurafac SLF-180, 4% Novel 1021 GB)) | | | | | | | | |
|---|---|---|---|---|---|---|---|---|
| ppm, Actives in Rinse Aid | 60 | 70 | 80 | 90 | 100 | 110 | 120 | 130 |
| Polycarbonate Tile (clear) New | | | 1 | 1 | 1 | 1 | 1 | 1 |
| Glass tumbler | | 1 | 1 | 1 | 1 | 1 | 1 | 1 |
| China Plate | | 1 | 1 | 1 | 1 | 1 | 1 | 1 |
| Melamine Plate | 1 | 1 | 1 | 1 | 1 | 1 | X | X |
| Polypropylene Cup (yellow) | | 1 | 1 | 1 | 1 | 1 | 1 | 1 |
| Dinex Bowl (blue) | | | | 1 | 1 | 1 | 1 | 1 |
| Polypropylene Jug (blue) | | 1 | 1 | 1 | 1 | 1 | 1 | 1 |
| Stainless Steel Knife | 1 | 1 | 1 | 1 | 1 | 1 | 1 | 1 |
| Polypropylene tray (peach) New | | 1 | 1 | 1 | 1 | 1 | 1 | 1 |
| Fiberglass tray (tan) New | | 1 | 1 | 1 | 1 | 1 | 1 | 1 |
| Stainless steel slide 316 New | 1 | 1 | 1 | 1 | 1 | 1 | X | X |
| Temperature, ° F. | 140° F. | 140° F. | 140° | 140° F. | 140° F. | 140° F. | 140° F. | 140° F. |
| Suds | 1/8" | 1/4" | 1/4" | 1/2" | 1/2" | 1/2" | 1/2-3/4" | 3/4" |

TABLE 8C

| (Control) | | | | | | | | |
|---|---|---|---|---|---|---|---|---|
| ppm, Actives in Rinse Aid | 60 | 70 | 80 | 90 | 100 | 110 | 120 | 130 |
| Polycarbonate Tile (clear) New | | 1 | 1 | 1 | 1 | 1 | 1 | 1 |
| Glass tumbler | | 1 | 1 | 1 | 1 | 1 | 1 | 1 |
| China Plate | | 1 | 1 | 1 | 1 | 1 | 1 | 1 |

TABLE 8C-continued (Control)

| ppm, Actives in Rinse Aid | 60 | 70 | 80 | 90 | 100 | 110 | 120 | 130 |
|---|---|---|---|---|---|---|---|---|
| Melamine Plate | 1 | 1 | 1 | 1 | 1 | 1 | 1 | 1 |
| Polypropylene Cup (yellow) |  | 1 | 1 | 1 | 1 | 1 | 1 | 1 |
| Dinex Bowl (blue) |  | 1 | 1 | 1 | 1 | 1 | 1 | 1 |
| Polypropylene Jug (blue) |  | 1 | 1 | 1 | 1 | 1 | 1 | 1 |
| Stainless Steel Knife |  | 1 | 1 | 1 | 1 | 1 | 1 | 1 |
| Polypropylene tray (peach) New |  | 1 | 1 | 1 | 1 | 1 | 1 | 1 |
| Fiberglass tray (tan) New |  | 1 | 1 | 1 | 1 | 1 | 1 | 1 |
| Stainless steel slide 316 New | 1 | 1 | 1 | 1 | 1 | 1 | 1 | 1 |
| Temperature, ° F. | 140° F. | 140° F. | 140° F. | 140° F. | 140° F. | 140° F. | 140° F. | 140° F. |
| Suds | Trace | Trace | Trace | Trace | Trace | Trace | Trace | Trace |

As set forth above in Tables 8, "1" represents "pin point" sheeting and an "X" corresponds to complete sheeting. Pinhole Sheeting—refers to the appearance of tiny pinholes on the surface of the water draining off of the ware wash material. These holes increase slightly in size as the water continues to drain off. No droplets should be left on the surface of the test material as the water nears being completely drained. Upon drying, no spots are left on the surface of the test pieces. Complete Sheeting—refers to an unbroken sheet of water clinging to the surface of the test material with no holes or breakage of the water surface as the water continues to drain. There is actually a micro thin layer of film on the water surface. As the water continues to drain, the film layer squeezes closer and closer to the dish. Upon opening the doors of the ware wash machine and exposing the dishes to the open air, all test materials immediately flash dry (<30 seconds for 160° F., <60 seconds for 120° F.), and no spots are left on the surface of the test materials.

As can be seen from these tables, the test formulations achieved either pin point or complete sheeting on all substrates whereas the comparative Control rinse aid composition, was only able to achieve pin point sheeting in these experiments.

In addition to evaluating the substrates for water sheeting, the level of foam present with each addition of rinse additive to the water was observed. The foam level in the dish machine was also noted. Foam levels of one-half inch or less are considered acceptable.

Example 5

Spot and film accumulation on ware was also evaluated using a ten-cycle spot and film test to assess the impact of rinse aids on the amount of spots and film that appear on hydrophilic and hydrophobic ware samples washed in an institutional type dish machine in the presence of detergent and food soil.

The ware wash machine was filled with water and the hardness was tested (17 gpg). The tank heaters were turned on and the ware wash machine wash cycle and rinse cycle temperatures were selected. The amount of detergent and food soil were weighed to charge the sump to reach desired concentrations of 1200 ppm Apex Detergent and 2000 ppm food soil. The amounts of detergent and food soil were weighted and put into 9 containers, respectively, in order to compensate for the loss from rinse water after each cycle. Drinking glasses, plastic tumblers, glass coupons and polycarbonate coupons were placed in the rack according to the positions shown below for 6 glasses (1-6), 3 polycarbonate coupons (7-9), for drying (residual water) 3 glasses (A-C), and 3 tumblers (D-F).

| 1 |   |   |   | A |
|---|---|---|---|---|
| 2 | 4 |   | B |   |
| 3 | 5 | 6 | C |   |
| 7 |   |   | D | E |
|   | 8 |   |   |   |
|   |   | 9 |   | F |

The machine rinse pump was primed to the desired dosage of rinse aid and the sump was primed with 1200 ppm detergent and 2000 ppm food soil. Put the rack in the ware wash machine for one cycle. Food soil and detergent (one of the nine containers measured ahead of time) was added after first cycle to compensate loss during the rinse cycle. Controls were run with no rinse aid and with benchmark rinse aid. Another cycle was started and repeated until ten cycles have been run totally. Then the wares A-F were sealed back to each plastic seal bag (where original pre-weights were obtained) and each weighed separately. Wares/coupons were dried overnight and then graded by image analysis and visual grading on spots and film. The wares are evaluated for appearance by trained personnel and by image analysis of digital photographs of the dried wares.

Figure 3A:
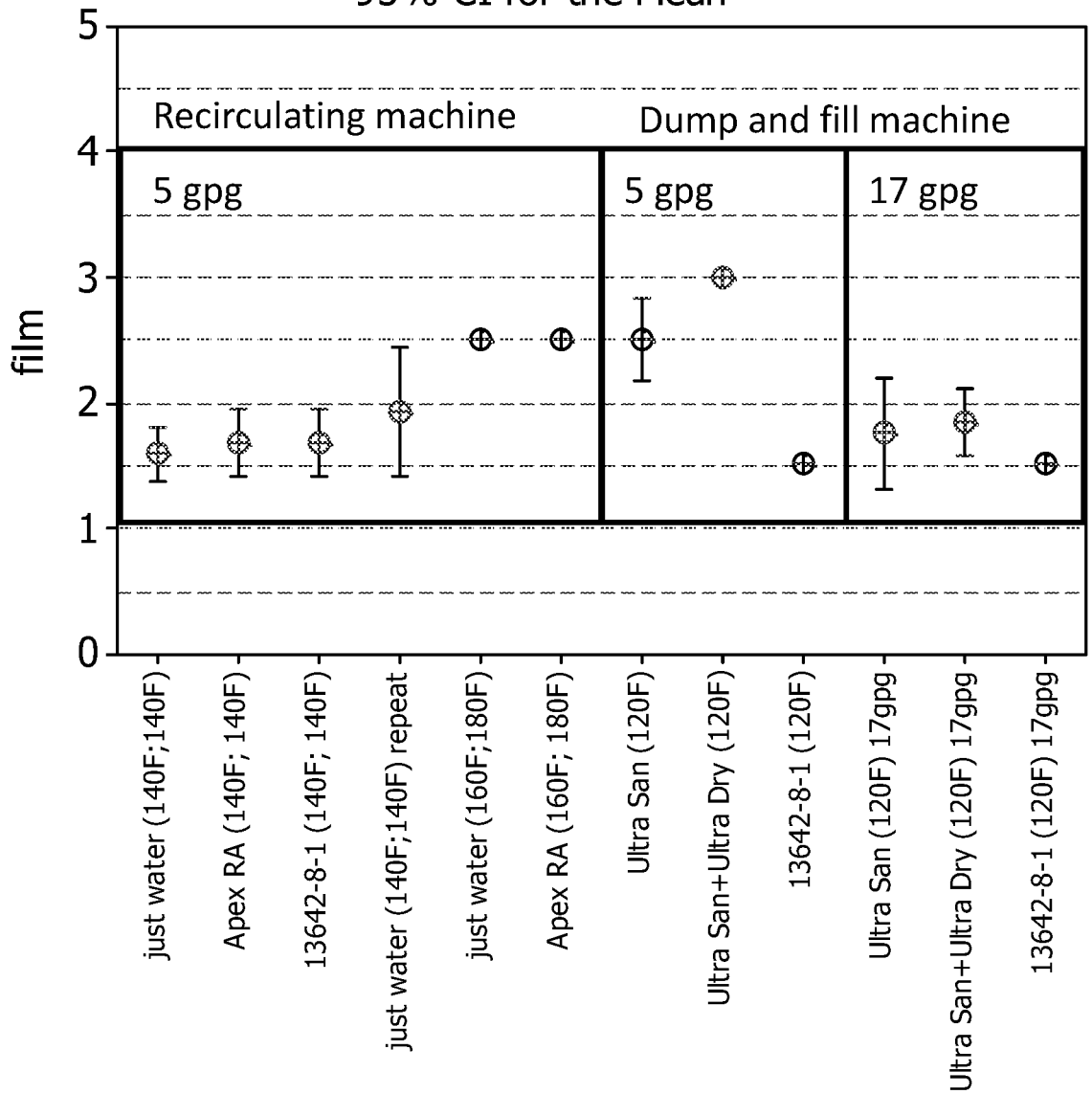
FIGS. 3A-3B show visual grading data of the glasses (FIG. 3A) and plastic coupons (FIG. 3B) for sanitizing rinse composition and for control samples set forth in the Examples according to embodiments of the invention.
Figure 3B:
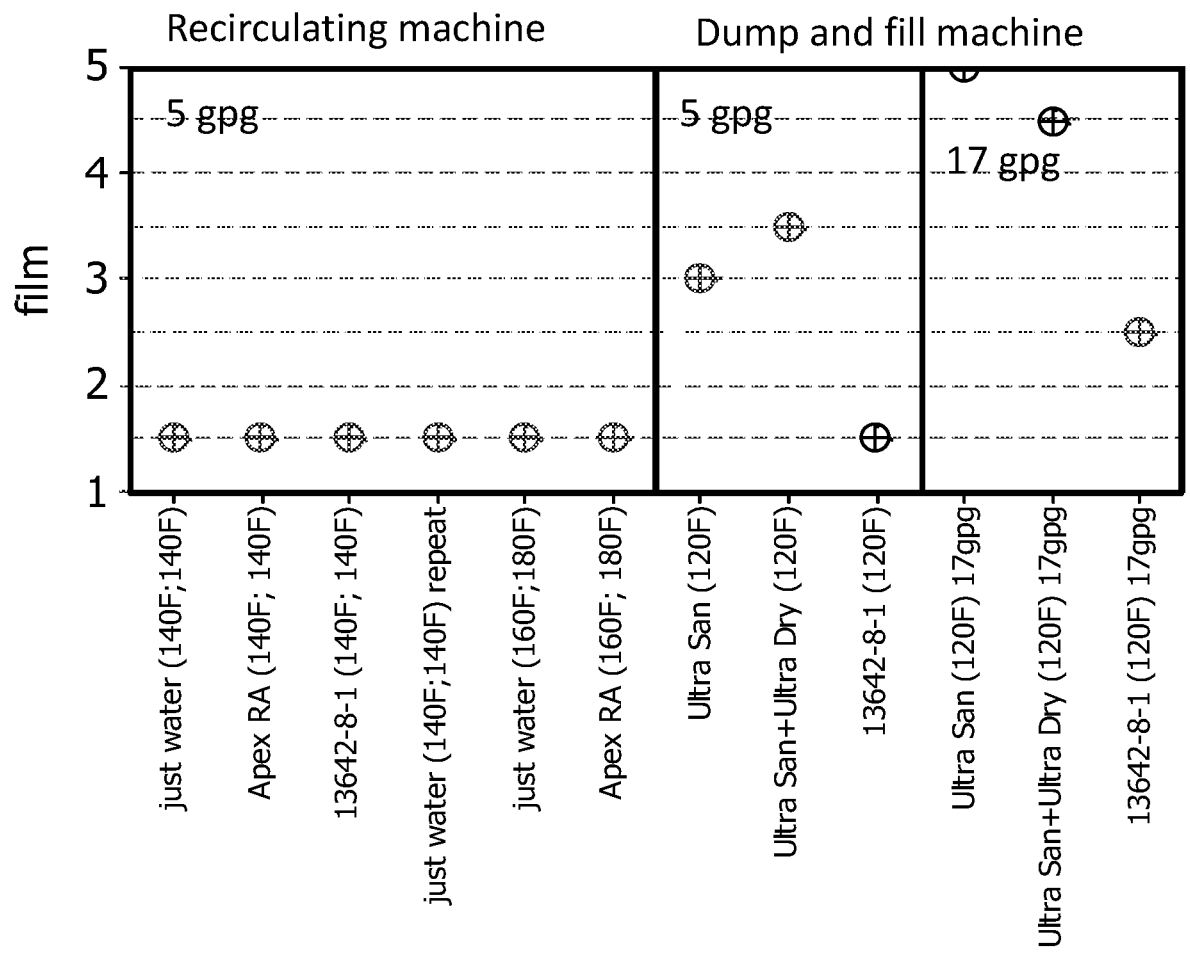

This test method was performed under conditions designed to replicate both "dump and fill" and "recirculating" type dish machines. The test formulation 13642-08-01 was compared to results obtained with various commercial rinse aid controls designed for each type of dish machine and water or water and chlorine bleach controls. Visual assessment of the results for both the glasses and plastic coupons treated with typical low temperature ware wash sanitizing and bleach (Ultra San, Ecolab Inc.) and with the sanitizing rinse aid composition 13642-08-01 (shown above in Table 4A) are provided in the grading results shown in FIGS. 3-4.

Figure 2A:
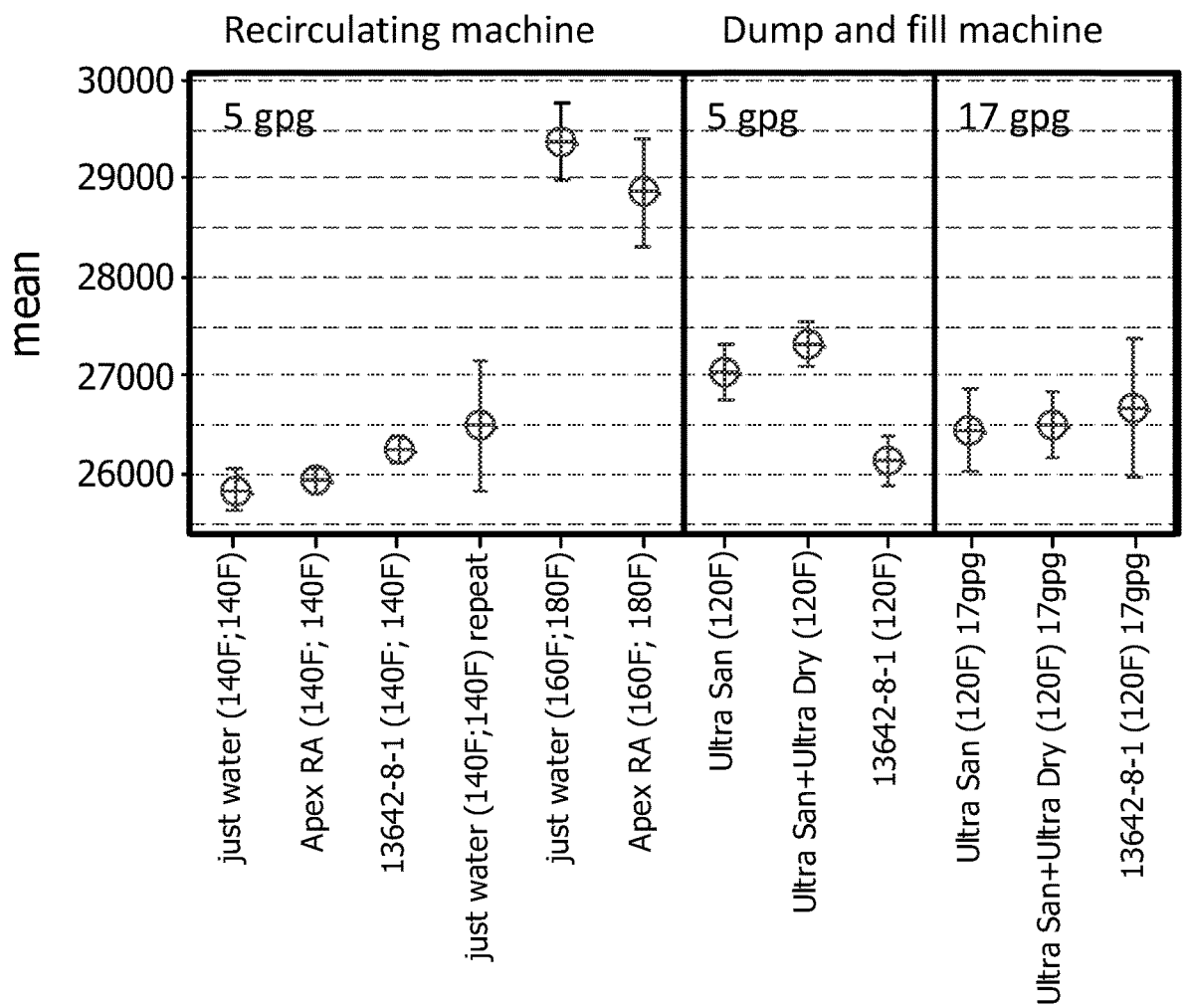
FIGS. 2A-2B show image analysis data of film on glasses (FIG. 2A) and plastic coupons (FIG. 2B) for sanitizing rinse composition and for control samples set forth in the Examples according to embodiments of the invention.
Figure 2B:
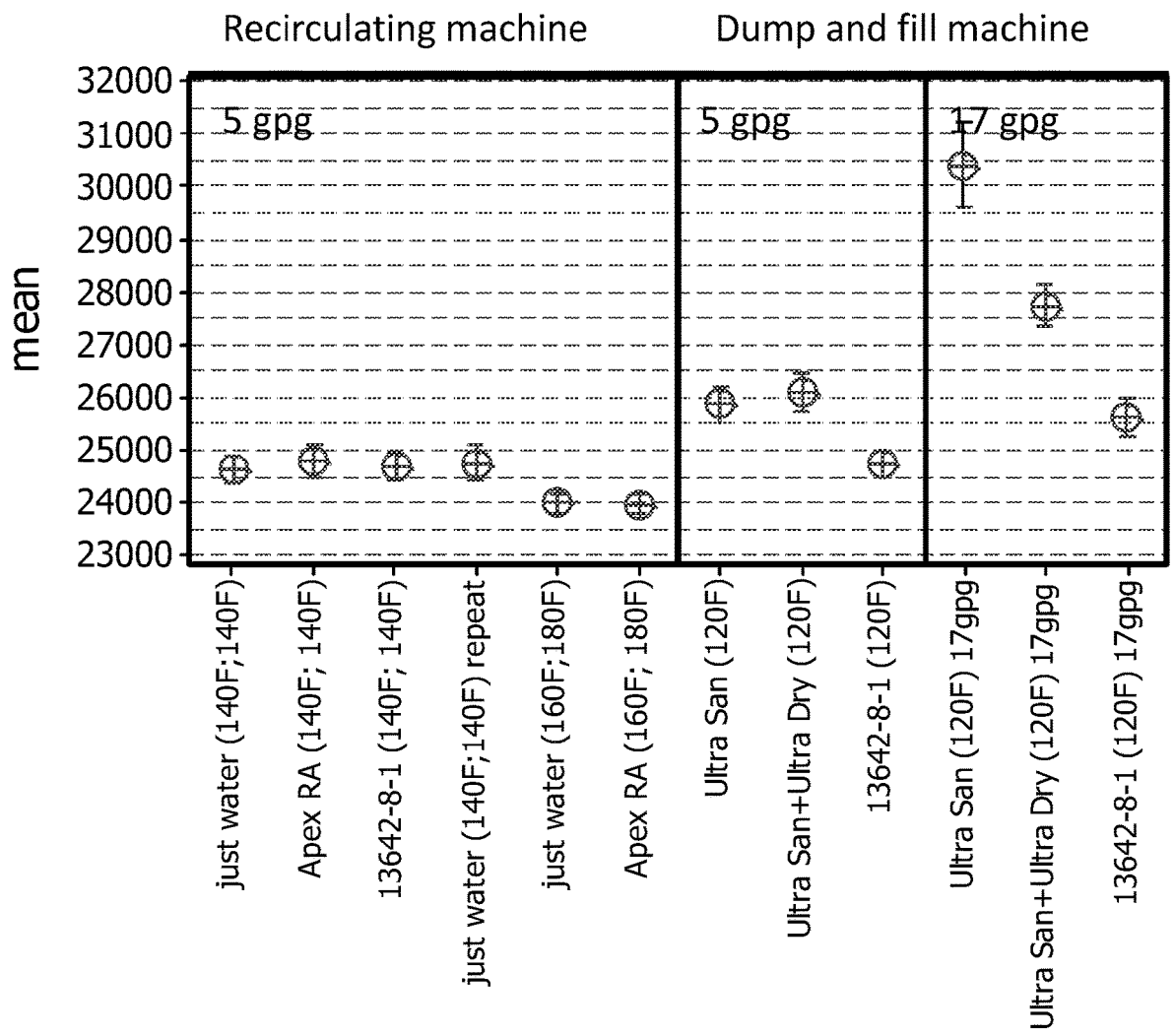

Image analysis data of film on glasses (FIG. 2A) and plastic coupons (FIG. 2B) for sanitizing rinse composition and for control samples using Apex Rinse Aid or Ultra San+Ultra dry. The image analysis data of the glasses and plastic coupons are shown for the glasses (FIG. 3A) and plastic coupons (FIG. 3B) for sanitizing rinse composition and for control samples using Apex Rinse Aid or Ultra San+Ultra dry.

Example 6

The antimicrobial efficacy of formulations according to embodiments of the invention were measured by AOAC test method 960.09, with modifications set forth in the description of the Example. The operating technique of the AOAC official method (960.09) for evaluating the antimicrobial efficacy of a food contact sanitizer requires 99 mL of the test biocide to be dispensed into a sterile 250 mL Erlenmeyer flask and then placed in a 77° F. (25° C.) water bath until it has temperature equilibrated, or 20 minutes, before starting the micro evaluation. The compositions described here are intended for use in mechanical dish machines and will be used at temperatures of approximately 120° F. to 140° F. To ensure the sanitizing rinse aid compositions according to the invention achieved required efficacy at these elevated application temperatures, the above mentioned food contact sanitizer method was modified to equilibrate 99 mL of a use-solution to 120° F., 130° F. or 140° F. Further, it was determined that minimal exposure to heated diluent was necessary to maintain an active level in solution high enough to achieve appropriate efficacy in suspension.

The modified use-solution preparation procedure is outlined herein: Test substance diluent was pre-heated and equilibrated to the test temperature. Sanitizing rinse aid was diluted in DI water to make a 1% (1.0 g/100 g total) stock solution. A stock solution was considered necessary to deliver an accurate weight of chemistry greater than 1 g per test flask. An appropriate amount of stock solution to achieve a final use-solution concentration of 8.3 ppm POOA was added to a 500 mL Erlenmeyer flask and diluted to a total weight of 500 g by the pre-heated diluent. While mixing, 99 mL of the sanitizing rinse aid use-solution were dispensed into three separate 250 mL Erlenmeyer test flasks. All three test flasks were placed in a test temperature equilibrated water bath at the same time. Flask #1 was designated for monitoring temperature, as well as use-solution active level. A thermometer was put in this flask to observe the temperature of the use-solutions. Once the temperature had reached the desired test temperature (+1° C.), the micro suspension study began on the other two test flasks (flasks #2 and #3) in the water bath. At the same time as the micro study, an additional analyst titrated flask #1 for use-solution active levels.

Antimicrobial efficacy data for lead sanitizing rinse aid compositions are shown in the Tables 9A-D.

TABLE 9A (replicate 1)

| Formula ID | Targeted Concentration (ppm POOA) | Titrated Concentration (ppm POOA) | Use-solution Temperature | Avg. Log$_{10}$ Reduction in 30 sec (E. coli) |
|---|---|---|---|---|
| 13642-08-01 Batch A | 8.3 ppm | 9.5 ppm | 118.4° F. | >7.03 |
|  |  | 8.1 ppm | 118.4° F. | >7.03 |
| 13642-08-01 Batch B |  | 7.41 ppm | 119.5° F. | >7.03 |
|  |  | 8.6 ppm | 117.9° F. | >7.03 |
| 13642-08-01 Batch C |  | 9.2 ppm | 118.8° F. | >7.03 |
|  |  | 7.8 ppm | 118.6° F. | >7.03 |

TABLE 9B (replicate 2)

| Formula ID | Targeted Concentration (ppm POOA) | Titrated Concentration (ppm POOA) | Use-solution Temperature | Avg. Log$_{10}$ Reduction in 30 sec (E. coli) |
|---|---|---|---|---|
| 13642-08-01 Batch A | 8.3 ppm | 7.81 ppm | 118.4° F. | 6.93 |
|  |  | 7.86 ppm | 118.4° F. | >6.93 |
| 13642-08-01 Batch B |  | 5.85 ppm | 119.5° F. | 5.76 |
|  |  | 7.86 ppm | 118.4° F. | 6.81 |
| 13642-08-01 Batch C |  | 7.74 ppm | 118.6° F. | 6.49 |
|  |  | 7.57 ppm | 118.4° F. | >6.93 |

TABLE 9C (Replicate #3*)

| Formula ID | Targeted Concentration (ppm POOA) | Use-solution Temperature | Avg. Log$_{10}$ Reduction in 30 sec | |
|---|---|---|---|---|
|  |  |  | S. aureus | E. coli |
| 13642-08-01 Batch A | 8.3 ppm | 120° F. | >6.90 | >7.08 |
| 13642-08-01 Batch B |  |  | >6.90 | >7.08 |
| 13642-08-01 Batch C |  |  | >6.90 | >7.08 |

*Performed by a second analyst. Titrations of the use-solution were not performed in this study; however the rest of the use-solution preparation method was followed.

TABLE 9D (Replicate #4)

| Formula ID | Targeted Concentration (ppm POOA) | Use-solution Temperature | Avg. Log$_{10}$ Reduction in 30 sec | |
|---|---|---|---|---|
|  |  |  | S. aureus | E. coli |
| 13642-08-01 Batch A | 8.3 ppm | 140° F. | >6.91 | >7.11 |
| 13642-08-01 Batch B |  |  | >6.91 | >7.11 |
| 13642-08-01 Batch C |  |  | >6.91 | >7.11 |

The data set forth in Table 9 shows that beneficially, according to the invention, there is a demonstrated synergy between the peroxycarboxylic acid antimicrobial efficacy and temperature, wherein improved antimicrobial efficacy at elevated temperatures allows formulation of a non-acidic peroxycarboxylic acid.

To further characterize the discovery that temperature greatly impacts efficacy of POOA against gram negative microorganisms such as E. coli, additional studies were performed at temperatures below 120° F. These data are collected in Table 10 below.

TABLE 10

| Formula ID | Concentration (ppm POOA) | Use-solution pH | Test Temp. | Avg. Log$_{10}$ Reduction in 30 sec | |
|---|---|---|---|---|---|
|  |  |  |  | S. aureus | E. coli |
| 13505-84-4 | 15 ppm | pH 7.30 | 77° F. | >6.47 | 1.24 |
|  | 20 ppm | pH 7.38 |  | >6.47 | 2.71 |
|  | 9.8 ppm | pH 7.48 | 100° F. | N/A | >6.75 |
|  | 8.6 ppm | pH 7.44 |  |  | >6.75 |

TABLE 10-continued

| Formula ID | Concentration (ppm POOA) | Use-solution pH | Test Temp. | Avg. Log$_{10}$ Reduction in 30 sec | |
|---|---|---|---|---|---|
| | | | | S. aureus | E. coli |
| | 9.8 ppm | pH 7.48 | 110° F. | | >6.75 |
| | 8.6 ppm | pH 7.44 | | | >6.75 |

The efficacy against *E. coli* was significantly less at room temperature than at increased temperatures of 100° F. and 110° F. Beneficially, the micro efficacy of the compositions are suitable for use, for example, in mechanical dish machines which are generally operated at temperatures of at least about 100° F., at least about 120° F. and/or at least about 140° F. (including all ranges disposed therein between). Use-solutions tested at elevated temperatures achieved complete kill of *E. coli* within 30 seconds at approximately half the concentration as room temperature tested use-solutions. These data support a synergist effect of increased temperature in combination with Sanitizing Rinse compositions described herein for efficacy at a neutral pH against *E. coli*. It is unexpected according to the invention that increasing temperature to at least about 100° F., at least about 110° F. and/or at least about 120° F. overcomes peroxyoctanoic acid efficacy dependence on pH.

As one skilled in the art shall ascertain from the disclosure of the invention, the sanitizing rinse aid compositions are particularly suited for microbial efficacy, including for example Gram negative pathogenic organisms, at temperatures of at least about 100° F., at least about 110° F. and/or at least about 120° F. In some aspects, the contact time for the sanitizing rinse aid composition is about 30 seconds (such as shown in the examples using U.S. EPA regulatory requirements for food contact sanitizing). However, in other aspects, the contact time for obtaining the measured microbial efficacy is less, such as about 15 seconds as may be applicable in various ware wash machines and applications of use thereof. In still further aspects, the contact time may be more than 15 seconds or more than 30 seconds depending upon a particular application of use.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method of sanitizing and rinsing comprising:
providing a low odor, liquid concentrate, equilibrium peroxycarboxylic acid sanitizing rinse aid composition, wherein the composition comprises: a $C_7$-$C_{22}$ peroxycarboxylic acid; a $C_7$-$C_{22}$ carboxylic acid; less than 2 wt-% of peroxyacetic acid and acetic acid; hydrogen peroxide; an alkyl-ethylene oxide-propylene oxide type nonionic surfactant; and an alcohol ethoxylate nonionic surfactant; and
sanitizing a surface in need thereof without an additional rinsing step;
wherein the composition when diluted from about 0.01% weight/volume to about 1% weight/volume provides at least a 5 log reduction in pathogenic organisms at a temperature of at least about 100° F.

2. The method of claim 1, wherein the composition is diluted from about 0.01% weight/volume to about 0.2% weight/volume with a diluent.

3. The method of claim 2, wherein the composition is diluted from about 0.01% weight/volume to about 0.05% weight/volume with a diluent.

4. The method of claim 2, wherein the sanitized surface is spot-free and film-free.

5. The method of claim 4, wherein the sanitizing is a low or no odor application of use.

6. The method of claim 1, wherein the utilities for a warewashing machine employing the sanitizing are substantially similar to or less than a low temperature ware wash machine employed for chlorine-based sanitizing.

7. The method of claim 1, wherein the $C_7$-$C_{22}$ peroxycarboxylic acid is a $C_8$ peroxycarboxylic acid and wherein the $C_7$-$C_{22}$ carboxylic acid is a $C_8$ carboxylic acid.

8. The method of claim 1, wherein the alkyl-ethylene oxide-propylene oxide type nonionic surfactant is according to the following structure alkyl-$(EO)_m$—$(PO)_n$—POH, wherein m is an integer in the range from 1 to 20 and n is an integer in the range from 1 to 20, and wherein the alcohol ethoxylate nonionic surfactant is according to the following structure R—O—$(CH_2CH_2O)_n$—H, wherein R is a $C_1$-$C_{12}$ alkyl group and n is an integer in the range of 1 to 100.

9. The method of claim 1, further comprising at least one additional agent selected from the group consisting of a hydrotrope or coupling agent, a solvent, a stabilizing agent and combinations thereof.

10. The method of claim 9, wherein the stabilizing agent is a phosphate peroxycarboxylic acid stabilizer and/or dipicolinic acid peroxycarboxylic acid stabilizer.

11. The method of claim 1, wherein the composition comprises from about 1 wt-% to about 40 wt-% of the $C_7$-$C_{22}$ peroxycarboxylic acid, from about 1 wt-% to about 80 wt-% of the $C_7$-$C_{22}$ carboxylic acid, from about 1 wt-% to about 80 wt-% of the hydrogen peroxide, and from about 1 wt-% to about 50 wt-% of the nonionic defoaming surfactant and the nonionic wetting surfactant.

12. The method of claim 1, wherein the composition when diluted from about 0.01% weight/volume to about 0.05% weight/volume provides at least a 5 log reduction in pathogenic organisms in 30 seconds or less at a temperature of at least about 120° F.

13. The method of claim 1, wherein the composition contains less than about 1 wt-% of peroxyacetic acid.

* * * * *